United States Patent [19]
Chang

[11] Patent Number: 5,912,326
[45] Date of Patent: Jun. 15, 1999

[54] CEREBELLUM-DERIVED GROWTH FACTORS

[75] Inventor: Han Chang, Mountain View, Calif.

[73] Assignees: President and Fellows of Harvard College, Cambridge, Mass.; Leland S. Stanford University, Palo Alto, Calif.

[21] Appl. No.: 08/525,864

[22] Filed: Sep. 8, 1995

[51] Int. Cl.$^6$ .......................... C12N 15/18; C07K 14/475
[52] U.S. Cl. ............................................ 530/399; 530/350
[58] Field of Search ...................................... 530/350, 399

[56] References Cited

U.S. PATENT DOCUMENTS

| | | |
|---|---|---|
| 5,237,056 | 8/1993 | Fischbach . |
| 5,367,060 | 11/1994 | Vandlen et al. . |
| 5,594,114 | 1/1997 | Goodearl et al. . |
| 5,602,096 | 2/1997 | Goodearl et al. . |
| 5,606,032 | 2/1997 | Goodearl et al. . |

FOREIGN PATENT DOCUMENTS

| | | |
|---|---|---|
| WO 91/18921 | 12/1991 | WIPO . |
| WO 92/12174 | 7/1992 | WIPO . |
| WO 92/18627 | 10/1992 | WIPO . |
| WO 92/20798 | 11/1992 | WIPO . |
| WO 94/00140 | 1/1994 | WIPO . |
| WO 94/03644 | 2/1994 | WIPO . |
| WO 94/04560 | 3/1994 | WIPO . |
| WO 94/08007 | 4/1994 | WIPO . |
| WO 94/28133 | 12/1994 | WIPO . |

OTHER PUBLICATIONS

Bacus, S. et al., "A Ligand for the erbB–2 Oncogene Product (gp30) Induces Differentiation of Human Breast Cancer Cells," *Cell Growth & Differentiation*, vol. 3, 401–411 (1992).

Ben–Baruch, N. and Yarden, Y., "Neu Differentiation Factors: A Family of Alternatively Spliced Neuronal and Mesenchymal Factors," *P.S.E.B.M.*, vol. 206, 221–227 (1994).

Chang, H. and Gilbert, W., "Cloning and Characterization of a New Factor Related to ARIA/NDF/GGF," *Society for Neuroscience Abstracts*, vol. 20, abstract No. 691.20, 1694 (1994).

Falls, D. et al., "ARIA, a Protein that Stimulates Acetylcholine Receptor Synthesis, is a Member of the Neu Ligand Family," *Cell*, vol. 72, 801–815 (1993).

Geistlich, A. and Gehring, H., "CDGF (Chicken Embryo Fibroblast–Derived Growth Factor) is Mitogenically Related to TGF–β and Modulates PDGF, bFGF, and IGF–I Action on Sparse NIH/3T3 Cells," *Experimental Cell Research*, vol. 204, 329–335 (1993).

Goodearl, A. et al., "Purification of Multiple Forms of Glial Growth Factor," *The Journal of Biological Chemistry*, vol. 268, No. 24, 18095–18102 (1993).

Ho, W. et al., "Sensory and Motor Neuron–derived Factor," *The Journal of Biological Chemistry*, vol. 270, No. 24, 14523–14532 (1995).

Holmes, W. et al., "Identification of Heregulin, a Specific Activator of p $185^{erbB2}$," *Science*, vol. 256, 1205–1210 (1992).

Huang, S. and Huang, J., "Purification and Characterization of the neu/erb B2 Ligand–Growth Factor from Bovine Kidney," *The Journal of Biological Chemistry*, vol. 267, No. 16, 11508–11512 (1992).

Küng, W. et al., "Isolation of a Heregulin–Like Growth Factor Secreted by Estrogen Receptor–Negative MDA–MB–231 Human Breast Cancer Cells that Stimulates Estrogen Receptor–Positive Cells," *Biochemical and Biophysical Research Communications*, vol. 202, No. 3, 1357–1365 (1994).

Lemke, G. and Brockes, J., "Identification and Purification of Glial Growth Factor," *The Journal of Neuroscience*, vol. 4, No. 1, 75–83 (1984).

Lupu, R. et al., "Direct Interaction of a Ligand for the erbB2 Oncogene Product with the EGF Receptor and $185^{erbB2}$," *Science*, vol. 249, 1552–1555, (1990).

Marchionni, M. et al., "Glial Growth Factors are Alternatively Spliced erbB2 Ligands Expressed in the Nervous System," *Nature*, vol. 362, 312–318 (1993).

Peles, E. et al., "Isolation of the Neu/HER–2 Stimulatory Ligand: A 44 kd Glycoprotein that Induces Differentiation of Mammary Tumor Cells," *Cell*, vol. 69, 205–216 (1992).

Peles, E. and Yarden, Y., "Neu and its Ligands: From an Oncogene to Neural Factors," *BioEssays*, vol. 15, No. 12, 815–824 (1993).

Prigent, S. and Lemoine, N., "The Type 1 (EGFR–Related) Family of Growth Factor Receptors and Their Ligands," *Progress in Growth Factor Research*, vol. 4, 1–24 (1992).

Wen, D. et al., "Neu Differentiation Factor: A Transmembrane Glycoprotein Containing and EGF Domain and an Immunoglobulin Homology Unit," *Cell*, vol. 69, 559–572 (1992).

Wen, D. et al., "Structural and Functional Aspects of the Multiplicity of Neu Differentiation Factors," *Molecular and Cellular Biology*, vol. 14, No. 3, 1909–1919 (1994).

*Primary Examiner*—Marianne P. Allen
*Attorney, Agent, or Firm*—Lahive & Cockfield, LLP; Giulio A. DeConti, Jr.

[57] ABSTRACT

The present invention relates to the discovery of a novel erbB receptor ligand, referred to hereinafter as "cdGF", which protein has apparently broad involvement in the formation and maintenance of ordered spatial arrangements of differentiated tissues in vertebrates, and can be used to generate and/or maintain an array of different vertebrate tissue both in vitro and in vivo.

11 Claims, 1 Drawing Sheet

CEREBELLUM-DERIVED GROWTH FACTORS

GOVERNMENT FUNDING

Work described herein was supported by National Institutes of Health Grant NIH EY08397 and NIH NS14506. The United States Government has certain rights in the invention.

BACKGROUND OF THE INVENTION

Pattern formation is the activity by which embryonic cells form ordered spatial arrangements of differentiated tissues. The physical complexity of higher organisms arises during embryogenesis through the interplay of cell-intrinsic lineage and cell-extrinsic signaling. Inductive interactions are essential to embryonic patterning in vertebrate development from the earliest establishment of the body plan, to the patterning of the organ systems, to the generation of diversive cell types during tissue differentiation (Davidson, E., (1990) *Development* 108: 365–389; Gurdon, J. B., (1992) *Cell* 68: 185–199; Jessell, T. M. et al., (1992) *Cell* 68: 257–270). The effects of developmental cell interactions are varied. Typically, responding cells are diverted from one route of cell differentiation to another by inducing cells that differ from both the uninduced and induced states of the responding cells (inductions). Sometimes cells induce their neighbors to differentiate like themselves (homoiogenetic induction); in other cases a cell inhibits its neighbors from differentiating like itself. Cell interactions in early development may be sequential, such that an initial induction between two cell types leads to a progressive amplification of diversity. Moreover, inductive interactions occur not only in embryos, but in adult cells as well, and can act to establish and maintain morphogenetic patterns as well as induce differentiation (J. B. Gurdon (1992) *Cell* 68: 185–199).

Many types of communication take place among animal cells during embryogenesis, as well as in the maintenance of tissue in adult animals. These vary from long-range effects, such as those of rather stable hormones circulating in the blood and acting on any cells in the body that possess the appropriate receptors, however distant they are, to the fleeting effects of very unstable neurotransmitters operating over distances of only a few microns. Of particular importance in development is the class of cell interactions referred to above as embryonic induction; this includes influences operating between adjacent cells or in some cases over greater than 10 cell diameters (Saxen et al. (1989) *Int J Dev Biol* 33: 21–48; and Gurdon et al. (1987) *Development* 99: 285–306). Embryonic induction is defined as in interaction between one (inducing) and another (responding) tissue or cell, as a result of which the responding cells undergo a change in the direction of differentiation. This interaction is often considered one of the most important mechanism in vertebrate development leading to differences between cells and to the organization of cells into tissues and organs.

Receptor tyrosine kinases are apparently involved in many different process including cellular differentiation, proliferation, embryonic development and, in some cases, neoplastic growth. High affinity binding of specific soluble or matrix-associated growth factor ligands can cause the activated receptor to associate with a specific repertoire of cytoplasmic signaling molecules that can lead to a cascade of intracellular signaling resulting in, for example, activation or inactivation of cellular gene programs involved in differentiation and/or growth. Accordingly, peptide growth factors that are ligands for such receptor tyrosine kinases are excellent candidates for intercellular signaling molecules with important developmental roles. Indeed, these ligands are known to have potent effects on a wide variety of cell activities in vitro, including survival, proliferation, differentiation, adhesion, migration and axon guidance. The powerful signaling effects of these molecules are further emphasized by the ability of both the ligands and the receptors, when activated by mutation or overexpression, to become potent oncogenes and cause drastic cellular transformation (reviewed by Cantley et al. (1991) *Cell* 64: 281–302; Schlessinger and Ullrich (1992) *Neuron* 9: 383–391; and Fantl et al. (1993) *Annu Rev Biochem* 62: 453–481).

To illustrate, specific developmental roles have been demonstrated for some growth factors or their tyrosine kinase receptors. For example, the c-kit receptor tyrosine kinase, encoded at the mouse W locus (Chabot et al. (1988) *Nature* 335: 88–89; and Geissler et al. (1988) *Cell* 55: 185–192) and its ligand KL, encoded at the mouse Sl locus (Flanagan and Leder (1990) *Cell* 63: 185–194; Copeland et al. (1990) *Cell* 63: 175–183; Huang et al. (1990) *Cell* 63: 225–233; and Zsebo et al. (1990) *Cell* 63: 213–224), determine the proliferation, survival, and/or migration of primordial germ cells, hematopoietic stem cells, and neural crest progenitor cells. Other examples are the trk family ligands and receptors, with highly specific functions in the developing mammalian nervous system (Klein et al. (1993) *Cell* 75: 113–122; and Jones et al. (1994) *Cell* 76: 989–999) and the FGF receptor, implicated in Xenopus mesoderm induction (Amaya et al. (1991) *Cell* 66: 257–270). In invertebrates, too, receptor tyrosine kinases and ligands such as sevenless, boss, torso, breathless and let-23 are known to play key roles in processes that range from setting up the primary embryonic axes to specifying the fate of a single cell in the ommatidium (Greenwald and Rubin (1992) *Cell* 68: 271–281; Shilo (1992) *Faseb J* 6: 2915–2922; and Zipursky et al. (1992) *Cold Spring Harbor Symp Quant Biol* 57: 381–389). Taken together, the emerging picture of the developmental functions of receptor tyrosine kinases and their ligands is striking in that these molecules play key roles at all stages of embryonic development, and in a remarkable range of different types of patterning process.

The receptor tyrosine kinases can be divided into families based on structural homology and, in at least some cases, obvious shared functional characteristics (Fantl et al. (1993) *Annu Rev Biochem* 62: 453–481). Remarkably, despite a number of members in the erbB family, all of these molecules were initially identified as orphan receptors without known ligands.

SUMMARY OF THE INVENTION

The present invention relates to the discovery of a novel erbB receptor ligand, referred to hereinafter as "cerebellum-derived growth factor" or "cdGF", which protein has apparently broad involvement in the formation and maintenance of ordered spatial arrangements of differentiated tissues in vertebrates, and can be used to generate and/or maintain an array of different vertebrate tissue both in vitro and in vivo.

In general, the invention features a cdGF polypeptide, preferably a substantially pure preparation of a cdGF polypeptide, or a recombinant cdGF polypeptide. In preferred embodiments the polypeptide has a biological activity associated with its binding to an erbB receptor, e.g., it retains the ability to bind to a erbB2, erbB3 or erbB4 receptor, though it may be able to either agonize or antagonize signal transduction by the erbB receptor. The polypeptide can be identical to the mammalian cdGF polypeptide (cdGF-1) shown in SEQ ID No: 2, or it can merely be homologous to that sequence. Likewise, the polypeptide can be identical to the mammalian cdGF polypeptide (cdGF-2) shown in SEQ ID No: 4 or 5, or it can merely be homologous to that sequence. For instance, the polypeptide preferably has an amino acid sequence at least 70% homologous to the amino acid sequence in either or both of SEQ ID Nos: 2 and 4, though higher sequence homologies of, for example, 80%, 85%, 90% or 95% are also contemplated. The polypeptide can comprise the full length protein represented in SEQ ID No: 2 or 4, or it can comprise a fragment of that protein, which fragment may be, for instance, at least 5, 10, 20, 50 or 100 amino acids in length. An exemplary fragment is shown in SEQ ID No. 5. A preferred cdGF polypeptide includes an EGF-like motif, such as the EGF-like motif including Cys253 through Cys289 of SEQ ID Nos: 2 or 4, or a sequence homologous thereto. Yet another preferred cdGF polypeptide includes a core sequence motif, such as a polypeptide including amino acid residues 143–314 of SEQ ID No. 2, or amino acid residues 143–330 of SEQ ID No. 4.

The polypeptide can be glycosylated, or, by virtue of the expression system in which it is produced, or by modification of the protein sequence to preclude glycosylation, reduced carbohydrate analogs can be provided. Likewise, cdGF polypeptides can be generated which lack an endogenous signal sequence (though this is typically cleaved off even if present in the pro-form of the protein), or which lack a transmembrane and cytoplasmic domain. In the instance of the latter, the removal of these C-terminal domains may result in a soluble form of the protein. In particular, polypeptides which lack amino acid residues C-terminal to Leu317 of SEQ ID No: 2 (the equivalent of cdGF-1 truncated at the transmembrane domain) are preferred, though polypeptides which are truncated anywhere between the equivalent of Cys289 and Thr318 of SEQ ID No: 2 are also contemplated. It is believed that the cdGF-2 mature amino acid sequence, which apparently lacks both a transmembrane domain and a cyctoplasmic domain, is soluble under certain conditions without further manipulation of the polypeptide sequence.

Furthermore, the cdGF polypeptide can include a secretion signal sequence, though mature cdGF polypeptides are also provided, such as by expression is a cell competent to remove the signal sequence. Exemplary mature forms of the subject cdGF polypeptides lack from 5 to 15 amino acid residues from the N-terminus of the polypeptide.

Moreover, as described below, the polypeptide can be either an agonist (e.g. mimics), or alternatively, an antagonist of a biological activity of a naturally occurring form of the protein, e.g., the polypeptide is able to modulate growth and/or differentiation of a cell which expresses an erbB receptor.

In a preferred embodiment, a peptide having at least one biological activity of the subject polypeptide may differ in amino acid sequence from the sequence in SEQ ID No: 2, 4 or 5, but such differences result in a modified protein which functions in the same or similar manner as a native cdGF protein or which has the same or similar characteristics of a native cdGF protein. However, homologs of the naturally occurring protein are contemplated which are antagonistic of the normal physiological role of the naturally occurring protein. For example, the homolog may be capable of interfering with the ability of naturally-occurring forms of cdGF to modulate gene expression, e.g. of developmentally or growth regulated genes.

In yet other preferred embodiments, the cdGF protein is a recombinant fusion protein which includes a second polypeptide portion, e.g., a second polypeptide having an amino acid sequence unrelated to cdGF, e.g. the second polypeptide portion is glutathione-S-transferase, e.g. the second polypeptide portion is an enzymatic activity such as alkaline phosphatase, and is a reagent for detecting cdGF receptors. In another embodiment, the second polypeptide sequence provides a cytotoxic or cytostatic protein which can be targeted to a cell by binding of the cdGF portion to its cognate receptors.

Yet another aspect of the present invention concerns an immunogen comprising a cdGF polypeptide in an immunogenic preparation, the immunogen being capable of eliciting an immune response specific for a cdGF polypeptide; e.g. a humoral response, e.g. an antibody response; e.g. a cellular response. In preferred embodiments, the immunogen comprising an antigenic determinant, e.g. a unique determinant, from a protein represented by SEQ ID No. 2 or SEQ ID No. 4.

A still further aspect of the present invention features an antibody preparation specifically reactive with an epitope of the cdGF immunogen.

Another aspect of the present invention provides a substantially isolated nucleic acid having a nucleotide sequence which encodes a cdGF polypeptide. In preferred embodiments: the encoded polypeptide specifically binds an erbB receptor protein and/or is able to either agonize or antagonize signal transduction events mediated by the erbB receptor. The coding sequence of the nucleic acid can comprise a sequence which can be identical to the coding sequence (or a portion thereof) of the cDNA shown in SEQ ID No: 1 or SEQ ID No: 3, or it can merely be homologous to that sequence. For instance, the cdGF encoding sequence preferably has a sequence at least 70% homologous to a nucleotide sequence of one or both of SEQ ID Nos: 1 and 3, though higher sequence homologies of, for example, 80%, 90% or 95% are also contemplated. The polypeptide encoded by the nucleic acid can comprise the amino acid sequence represented in SEQ ID No: 2 or 4, which is the full length protein, or it can comprise a fragment of that nucleic acid, which fragment may be, for instance, at least 5, 10, 20, 50 or 100 amino acids in length (such as the cdGF-2 fragment of SEQ ID No. 5). The polypeptide encoded by the nucleic acid can be either an agonist (e.g. mimics), or alternatively, an antagonist of a biological activity of a naturally occurring form of the protein.

Furthermore, in certain preferred embodiments, the subject cdGF nucleic acid will include a transcriptional regulatory sequence, e.g. at least one of a transcriptional promoter or transcriptional enhancer sequence, which regulatory sequence is operably linked to the cdGF gene sequence. Such regulatory sequences can be used in to render the cdGF gene sequence suitable for use as an expression vector.

In a further preferred embodiment, the nucleic acid hybridizes under stringent conditions to a nucleic acid probe corresponding to at least 12 consecutive nucleotides of SEQ ID No: 1; preferably to at least 20 consecutive nucleotides of SEQ ID No: 1; more preferably to at least 40 consecutive nucleotides of SEQ ID No: 1. For instance, nucleic acid are provided which specifically hybridize to nucleotides 180–605 (corresponding to Spacer 1) and/or nucleotides 870–929 (corresponding to Spacer 2) of SEQ ID No. 1, or sequences complementary thereto.

In yet a further preferred embodiment, the nucleic acid hybridizes under stringent conditions to a nucleic acid probe corresponding to at least 12 consecutive nucleotides of SEQ ID No: 3; preferably to at least 20 consecutive nucleotides of SEQ ID No: 3; more preferably to at least 40 consecutive nucleotides of SEQ ID No: 3. For instance, nucleic acid are provided which specifically hybridize to nucleotides 1–426 (corresponding to Spacer 1) and/or nucleotides 691–750 (corresponding to Spacer 2) of SEQ ID No. 1, or sequences complementary thereto.

The invention also features transgenic non-human animals, e.g. mice, rats, rabbits, chickens, frogs or pigs, having a transgene, e.g., animals which include (and preferably express) a heterologous form of a cdGF gene described herein, or which misexpress an endogenous cdGF gene, e.g., an animal in which expression of the subject cdGF protein is disrupted. Such a transgenic animal can serve as an animal model for studying cellular and tissue disorders comprising mutated or mis-expressed cdGF alleles or for use in drug screening.

The invention also provides a probe/primer comprising a substantially purified oligonucleotide, wherein the oligonucleotide comprises a region of nucleotide sequence which hybridizes under stringent conditions to at least 10 consecutive nucleotides of sense or antisense sequence of SEQ ID No: 1 and/or 3, or naturally occurring mutants thereof. In preferred embodiments, the probe/primer further includes a label group attached thereto and able to be detected. The label group can be selected, e.g., from a group consisting of radioisotopes, fluorescent compounds, enzymes, and enzyme co-factors. Probes of the invention can be used as a part of a diagnostic test kit for identifying transformed cells, such as for detecting in a sample of cells isolated from a patient, a level of a nucleic acid encoding the subject cdGF proteins; e.g. measuring the cdGF mRNA level in a cell, or determining whether the genomic cdGF gene has been mutated or deleted. Preferably, the oligonucleotide is at least 10 nucleotides in length, though primers of, for example, 20, 30, 50, 100, or 150 nucleotides in length are also contemplated.

In yet another aspect, the invention provides an assay for screening test compounds for inhibitors, or alternatively, potentiators, of an interaction between cdGF and an erbB receptor. An exemplary method includes the steps of (i) combining an erbB receptor, an cdGF polypeptide, and a test compound, e.g., under conditions wherein, but for the test compound, the cdGF protein and the erbB receptor are able to interact; and (ii) detecting the formation of a complex which includes the cdGF protein and the receptor. A statistically significant change, such as a decrease, in the formation of the complex in the presence of a test compound (relative to what is seen in the absence of the test compound) is indicative of a modulation, e.g., inhibition, of the interaction between cdGF and the receptor. For example, primary screens are provided in which the cdGF protein and the receptor protein are combined in a cell-free system and contacted with the test compound; i.e. the cell-free system is selected from a group consisting of a cell lysate and a reconstituted protein mixture.

Another aspect of the present invention relates to a method of inducing and/or maintaining a differentiated state, causing proliferation, and/or enhancing survival of a cell responsive to a cdGF protein, by contacting the cells with a cdGF agonist or a cdGF antagonist. For example, the present method is applicable to cell culture technique, such as in the culturing of neuronal and other cells whose survival or differentiative state is dependent on cdGF function. Moreover, cdGF agonists and antagonists can be used for therapeutic intervention, such as to enhance survival and maintenance of neurons and other neural cells in both the central nervous system and the peripheral nervous system, as well as to influence other vertebrate organogenic pathways, such as other ectodermal patterning, as well as certain mesodermal and endodermal differentiation processes.

Another aspect of the present invention provides a method of determining if a subject, e.g. a human patient, is at risk for a disorder characterized by unwanted cell proliferation or adherent control of differentiation. The method includes detecting, in a tissue of the subject, the presence or absence of a genetic lesion characterized by at least one of (i) a mutation of a gene encoding a cdGF protein, e.g. represented in SEQ ID No: 2 or 4, or a homolog thereof; or (ii) the mis-expression of a cdGF gene. In preferred embodiments, detecting the genetic lesion includes ascertaining the existence of at least one of: a deletion of one or more nucleotides from a cdGF gene; an addition of one or more nucleotides to the gene, a substitution of one or more nucleotides of the gene, a gross chromosomal rearrangement of the gene; an alteration in the level of a messenger RNA transcript of the gene; the presence of a non-wild type splicing pattern of a messenger RNA transcript of the gene; or a non-wild type level of the protein.

For example, detecting the genetic lesion can include (i) providing a probe/primer including an oligonucleotide containing a region of nucleotide sequence which hybridizes to a sense or antisense sequence of a cdGF gene, e.g. the nucleic acid represented in SEQ ID No: 1, 3 or 5, or naturally occurring mutants thereof or 5' or 3' flanking sequences naturally associated with the cdGF gene; (ii) exposing the probe/primer to nucleic acid of the tissue; and (iii) detecting, by hybridization of the probe/primer to the nucleic acid, the presence or absence of the genetic lesion; e.g. wherein detecting the lesion comprises utilizing the probe/primer to determine the nucleotide sequence of the cdGF gene and, optionally, of the flanking nucleic acid sequences. For instance, the probe/primer can be employed in a polymerase chain reaction (PCR) or in a ligation chain reaction (LCR). In alternate embodiments, the level of cdGF protein is detected in an immunoassay using an antibody which is specifically immunoreactive with a cdGF protein.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I–IV (D. M. Weir and C. C. Blackwell, eds., 1986); *Manipulating the Mouse Embryo,* (Cold Spring Harbor Laboratory Press, Cold Spring Harbor, N.Y., 1986).

Other features and advantages of the invention will be apparent from the following detailed description, and from the claims.

DETAILED DESCRIPTION OF THE INVENTION

Figure 1:
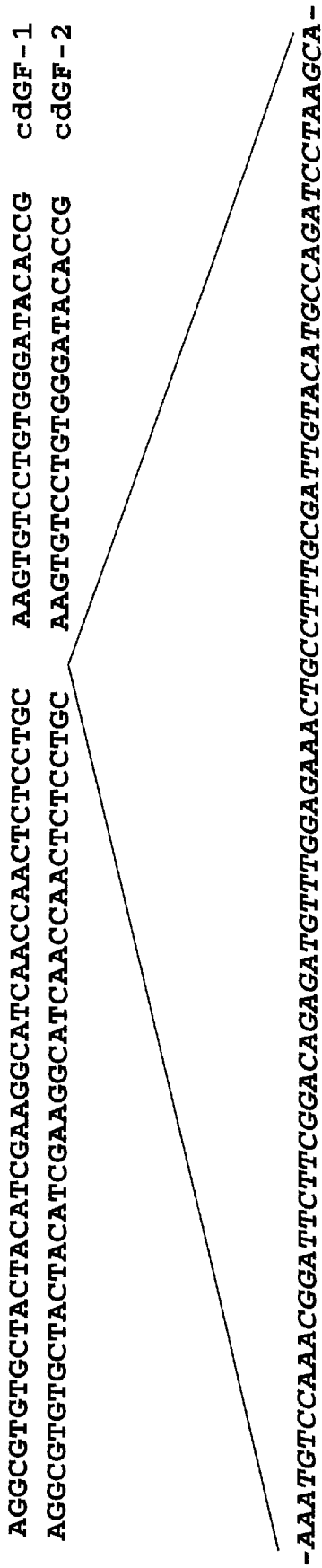
FIG. 1 is an nucleotide sequence alignment between portions of cdGF-1 and cdGF-2, illustrating the splicing variation between the two (SEQ ID NOS. 17 and 18).

Growth factors that are ligands for receptor tyrosine kinases control a wide variety of cellular activities. Virtually all of these ligands that have been characterized are known to have important functions in development and/or physiology and, in at least some cases, to be useful clinically. The existence of many additional, hitherto unidentified ligands is implied by the discovery over the last few years of a large number of tyrosine kinases that appear by their structure to be cell surface receptors, yet have no known ligand. The rapid discovery of these orphan receptors has been possible mostly through the application of techniques such as polymerase chain reaction that take advantage of the strong sequence conservation of the kinase catalytic domain. However, in contrast, identification of the ligands for the receptor tyrosine kinases has been more problematic.

It is also generally accepted that intercellular signaling plays a key role throughout vertebrate development. A great deal of progress has been made in understanding signals that mediate some of the earliest patterning events. However, that regulate many of the important regulate many of the important events that unfold as gastrulation and early organogenesis proceed, particularly the cell-cell signaling molecules that control the expression of gene programs. Protein tyrosine kinase receptors, such as members of the erbB family of receptors (e.g., erbB1, erbB2, erbB3, erbB4, etc.) have been especially intriguing in this regard, particularly because the expression domains for several of these receptors include these stages of development.

The expression patterns determined for some of the erbB family receptors have implied important roles for these molecules in early vertebrate development. In particular, the timing and pattern of expression the receptors during the phase of gastrulation and early organogenesis has suggested functions for these receptors in the important cellular interactions involved in patterning the embryo at this stage. Moreover, erbB receptors have been implicated, by their pattern of expression, in the development and maintenance of nearly every tissue in the embryonic and adult body. For instance, erbB receptors have been detected throughout the nervous system, the testes, the cartilaginous model of the skeleton, tooth primordia, the infundibular component of the pituitary, various epithelial tissues, lung, pancreas, liver and kidney tissues.

Observations such as this have been indicative of important and unique roles for erbB family of receptor kinases in development and physiology, but further progress in understanding their action has been severely limited by the lack of information on their ligands. To date, only a few ligands have been identified. For instance, it has been recently reported that a 45 kD protein heregulin-α (HRG-α) has been cloned from an mRNA-derived MDA-MB231 cell library. In addition, several complementary DNA clones encoding related HRGs were also identified, all the HRGs being similar to some extent to proteins in the epidermal growth factor (EGF) family (Holmes et al. 1992 $Nature$ 256: 1205). It has also been reported that a 44 kD glycoprotein secreted by transformed rat fibroblasts, termed Neu differentiation factor (NDF), has been cloned and expressed (Wen et al. 1992 $Cell$ 69: 559), and binds to an erbB receptor. Other molecules which have been identified as erbB ligands include the acetylcholine receptor inducing activity ("ARIA", Corfas et al. (1993) $PNAS$ 90: 1624–1628) and glial growth factor (GGF, Marchionni et al. (1993) $Nature$ 362: 312–328).

As described in the appended examples, a novel erbB receptor ligand has been cloned and is termed herein "cerebellum-derived growth factor" (cdGF). This protein, of which at least two isoforms exist, shares only about 50 percent homology with any of the ARIA, heregulin, NDF or GGF proteins. The cdGF protein interacts with certain erbB receptors. For instance, recombinant forms of the protein were produced from COS-7 cells, with the results indicating that the molecule can induce tyrosine phosphorylation of a 185 kD protein in MDA-MB 453 cells.

In addition to identifying this ligand and homologs thereof, the spatial distribution of expression of the protein in a number of different tissues has been carried out, and suggest that it is probable that cdGF is of central importance in development and maintenance of a variety of both neural and non-neural tissue. Given the apparent role of the cdGF protein in mediating inductive signals between tissues, the present data suggests that this protein is an important therapeutic target for modulating growth and developmental gene programs. For example, binding of a cdGF polypeptide of the present invention with an erbB receptor can be important for initiating and establishing diverse programs of growth or differentiation; as well as for providing a mechanism to ensure developmentally coordinated tissue patterning.

Moreover, it is suggested that certain erbB receptors, e.g. the erbB2 and/or erbB4 receptors, may also play a role in tumorogenesis. Consequently, the interaction of an erbB receptor with the subject cdGF polypeptides may be significant in the modulation of cellular homeostasis, in the control of organogenesis, or in the maintenance of differentiated tissues, as well as in the development of lymphocytic leukemias and other neoplastic disorders.

Accordingly, certain aspects of the present invention relate to diagnostic and therapeutic assays and reagents for detecting and treating disorders involving abherent expression of cdGF. Moreover, drug discovery assays are provided for identifying agents which can modulate the binding of cdGF with erbB receptors. Such agents can be useful therapeutically to alter the growth and/or differentiation of a cell. Other aspects of the invention are described below or will be apparent to those skilled in the art in light of the present disclosure.

For convenience, certain terms employed in the specification, examples, and appended claims are collected here.

The term "cdGF polypeptide" refers to a family of polypeptides characterized at least in part by being identical or sharing a degree of sequence homology with all or a portion of the polypeptides represented in SEQ ID Nos. 2, 4 and 5. The cdGF polypeptides can be cloned or purified from any of a number of eukaryotic organisms, especially vertebrates, and particularly mammals (including humans). Moreover, other cdGF polypeptides can be generated according to the present invention, which polypeptides do not ordinarily exist in nature, but rather are generated by non-natural mutagenic techniques.

Figure 2:
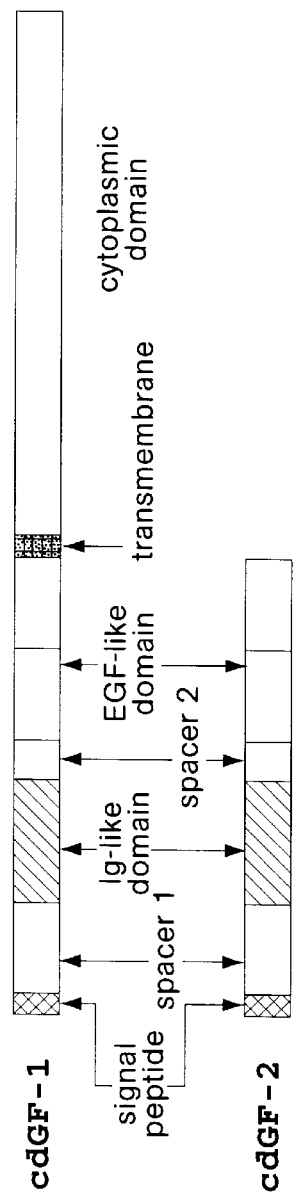
FIG. 2 is a schematic representation of the structural domains and motifs of cerebellum-derived growth factor.

From analysis of various clones isolated by protocols described in the appended examples, the cdGF proteins are inclusive of at least two alternate splicing forms. The transcript corresponding to the "cdGF-1" form provides an open reading frame which encodes a protein (see FIG. 2) having an extracellular domain (Met1-Lys314), a transmembrane domain (Thr318-Lys339), and a cytoplasmic domain (Thr340-Leu754). A dibasic sequence (K314/R315) is located adjacent to the transmembrane domain, indicating that proteolytic cleavage and release of the extracellular domain is likely.

The open reading frame of the "cdGF-2" transcript, on the other hand, encodes a protein which is truncated shortly after the EGF-like motif in the extracellular domain, presumably producing a protein which, by lacking a transmembrane domain and a cytoplasmic domain, is likely a soluble form of the protein. It is noted in FIG. 1 that the insertion of a 77 nucleotide sequence gives rise to frame shift just 3' prime to the end of the EGF-like domain, with a stop codon occurring in-frame shortly thereafter.

A number of features of this family of proteins can be observed from comparison of various cdGF polypeptides with each other and with other erbB receptor ligands. In particular, I have noted that the ectodomains of the cdGF proteins contain six cysteine residues which are apparently conserved with approximately the same characteristic spacing within the primary sequence of each of the known erbB receptor ligands. This "EGF-like" motif may represent a fragment which retains certain biological activities of the full length (mature) protein, such as, for example, the ability to bind an erbB receptor. In exemplary cdGF polypeptides, the EGF-like motif is represented by residues Cys253-Cys289 of SEQ ID No. 2 (cdGF-1) and SEQ ID No. 4 (cdGF-2). In addition to the EGF-like domain, both cdGF proteins identified contain an immunoglobulin-like domain (Thr143-Val230), as well as two stretches of amino acid residues in the amino terminal half of the extracellular domain, referred to herein as "spacer-1", corresponding to Met1-Ala142 of SEQ ID Nos. 2 and 4, and "spacer-2", corresponding to Arg231-Arg251 of SEQ ID Nos. 2 and 4 (see FIG. 2). In addition to these features which characterize the extracellular domain of cdGF, the full length protein also includes a transmembrane domain and a cytoplasmic domain.

The cysteinyl-bounded core amino acid sequence of the EGF family of mitogens has the consensus sequence $CY_1CY_2CY_3CY_4CY_5C$ (SEQ ID No: 7), where C is a cysteine, $Y_1$ represents 7 amino acids which can be the same or different, $Y_2$ represents 4 to 5 amino acids which can be the same or different, $Y_3$ represents 10 to 13 amino acids which can be the same or different, $Y_4$ represents any amino acid, and $Y_5$ represents 8 amino acids which can be the same or different, and is generally 36–40 residues in length. Based on this general arrangement of cysteine residues, a closely related motif, termed EGF-like motif, has been identified in a number of proteins. As used herein, an "EGF-like" amino acid sequence is represented by the general formula $CX_1CX_2CX_3CX_4CX_5C$ (SEQ ID No: 8), where C is a cysteine, $X_1$ represents 4 to 14 amino acids which can be the same or different, $X_2$ represents 3 to 8 amino acids which can be the same or different, $X_3$ represents 4 to 14 amino acids which can be the same or different, $X_4$ is any amino acid, and $X_5$ represents 8 to 14 amino acids which can be the same or different.

Finally, co- and post-translational modified forms of cdGF polypeptides are contemplated by the present invention. A "mature" cdGF polypeptide refers to a cdGF polypeptide which lacks a signal sequence (e.g., a peptidyl portion which causes extracellular secretion of at least a portion of the protein).

A "glycosylated" cdGF polypeptide is a cdGF polypeptide having a covalent linkage with a glycosyl group (e.g. a derivatized with a carbohydrate). For instance, the exemplary cdGF-1 and cdGF-2 proteins contain potential Asn-linked glycosylation sites. To generate an unglycosylated cdGF polypeptide, the polypeptide can be expressed in a system which is defective for glycosylation, such as a bacterial cell. Alternatively, an existing glycosylation site can be mutated to preclude carbohydrate attachment. Likewise, new glycosylation sites, such as for N-linked or O-linked glycosylation, can be added by recombinant techniques.

As used herein, the terms "erbB receptor" or "erbB-type receptor" refer to a class of receptor tyrosine kinases, comprising at least three paralogous genes, though many more orthologs exist within this class, e.g. homologs from different species. The erbB receptors, in general, are a discrete group of receptors related by homology and easily reconizable, e.g., they are typically characterized by an extracellular domain containing a characteristic spacing of cysteine residues, a hydrophobic transmembrane domain, and an intracellular region containing a highly conserved tyrosine kinase domain. Exemplary erbB receptors include the erbB2, erbB3 and erbB4 receptors. The term "erbB receptor" refers to the membrane form of the receptor protein, as well as soluble extracellular fragments which retain the ability to bind the ligand(s) of the present invention.

The term "ortholog" refers to genes or proteins which are homologs via speciation, e.g., closely related and assumed to have common descent based on structural and functional considerations. Orthologous proteins function as recognizably the same activity in different species.

The term "paralog" refers to genes or proteins which are homologs via gene duplication, e.g., duplicated variants of a gene within a genome. See also, Fritch, WM (1970) *Syst Zool* 19: 99–113.

The phrases "modifies cellular activities" and "modulates cellular activities", with respect to the biological activity of the subject cdGF polypeptides, refers to changes which occur in a cell due to activation of intracellular signals, e.g., primary or secondary, by cdGF interaction with other cellular proteins. For example, such cellular activities which may be affected by cdGF include proliferation, differentiation or survival of a cell, as well as cell-cell adhesion and other alterations in phenotype. In one aspect, the cellular activities which can be modified by a cdGF polypeptide pertain to maintenance of neuronal connections. In general, the cellular modifications can be the relatively-direct biochemical consequence of signal transduction events, or can be caused more indirectly, such as cdGF dependent activation or inactivation of particular genes or gene programs. A cdGF polypeptide which "modifies" cellular activities can refer to homologs which either mimic (e.g., agonize) or inhibit (e.g., antagonize) the normal response of a cell to the wild-type form of the protein.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "gene" or "recombinant gene" refers to a nucleic acid comprising an open reading frame encoding a cdGF polypeptide of the present invention, including both exon and (optionally) intron sequences. A "recombinant gene" refers to nucleic acid encoding a cdGF polypeptide and comprising cdGF-encoding exon sequences, though it may optionally include intron sequences which are either derived from a chromosomal cdGF gene or from an unrelated chromosomal gene. An exemplary recombinant gene encoding a subject cdGF polypeptide is represented by SEQ ID No: 1; yet another is represented by SEQ ID No: 3, still another is represented by SEQ ID No: 5. The term "intron" refers to a DNA sequence present in a given cdGF gene which is not translated into protein and is generally found between exons.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a cdGF polypeptide or, where anti-sense expression occurs from the transferred gene, the expression of a naturally-occurring form of the cdGF protein is disrupted.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of a recombinant cdGF gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of the cdGF protein.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of neural origin, e.g. neuronal cells. The term also covers so-called "leaky" promoters, which regulate expression of a selected DNA primarily in one tissue, but cause expression in other tissues as well.

As used herein, a "transgenic animal" is any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by micro-injection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of the subject cdGF protein, e.g. either agonistic or antagonistic forms. However, transgenic animals in which the recombinant cdGF gene is silent are also contemplated, as for example, the FLP or CRE recombinase dependent constructs described below. The "non-human animals" of the invention include vertebrates such as rodents, non-human primates, sheep, dog, cow, chickens, amphibians, reptiles, etc. Preferred non-human animals are selected from the rodent family including rat and mouse, most preferably mouse, though transgenic amphibians, such as members of the Xenopus genus, and transgenic chickens can also provide important tools for understanding, for example, embryogenesis. The term "chimeric animal" is used herein to refer to animals in which the recombinant gene is found, or in which the recombinant is expressed in some but not all cells of the animal. The term "tissue-specific chimeric animal" indicates that the recombinant cdGF gene is present and/or expressed in some tissues but not others.

As used herein, the term "transgene" means a nucleic acid sequence (encoding, e.g., a cdGF polypeptide), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding a cdGF polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a protein with the same biological activity.

"Homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 10 percent identity, though preferably less than 5 percent identity, with a cdGF sequence of the present invention.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding the subject cdGF polypeptide with a second amino acid sequence defining a domain foreign to and not substantially homologous with any domain of the cdGF protein. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula X-GF-Y, wherein GF represents a portion of the protein which is derived from a cdGF protein, and X and Y are independently absent or represent amino acid sequences which are not related to a cdGF sequence.

The term "evolutionarily related to", with respect to nucleic acid sequences encoding a cdGF polypeptide, refers to nucleic acid sequences which have arisen naturally in an organism, including naturally occurring mutants. The term also refers to nucleic acid sequences which, while derived from a naturally occurring cdGF gene, have been altered by mutagenesis, as for example, the combinatorial mutagenic techniques described below, yet still encode polypeptides which have at least one activity of a cdGF polypeptide.

The term "isolated" as also used herein with respect to nucleic acids, such as DNA or RNA, refers to molecules separated from other DNAs, or RNAs, respectively, that are present in the natural source of the macromolecule. For example, an isolated nucleic acid encoding the subject cdGF polypeptides preferably includes no more than 10 kilobases (kb) of nucleic acid sequence which naturally immediately flanks the cdGF gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

As described below, one aspect of the invention pertains to an isolated nucleic acid comprising the nucleotide sequence encoding a cdGF polypeptide, and/or equivalents of such nucleic acids. The term nucleic acid as used herein is intended to include fragments as equivalents. The term equivalent is understood to include nucleotide sequences encoding functionally equivalent cdGF polypeptides or functionally equivalent peptides which, for example, retain the ability to bind to an tyrosine kinase receptor of the erbB family, e.g. to the erbB2 and/or erbB4 receptors. Equivalent nucleotide sequences will include sequences that differ by one or more nucleotide substitutions, additions or deletions, such as allelic variants; and will, therefore, include sequences that differ from the nucleotide sequence of the cdGF genes shown in SEQ ID Nos: 1 or 3 due to the degeneracy of the genetic code. Equivalents will also include nucleotide sequences that hybridize under stringent conditions (i.e., equivalent to about 20–27° C. below the melting temperature ($T_m$) of the DNA duplex formed in about 1M salt) to a nucleotide sequence represented by SEQ ID No: 1 and/or 3. In preferred embodiments, equivalents includes nucleic acid sequences derived from and evolutionarily related to, a nucleotide sequences shown in any of SEQ ID No: 1 or 3.

Moreover, it will be generally appreciated that, under certain circumstances, it may be advantageous to provide, homologs of the subject cdGF polypeptide which function in a limited capacity as one of either a cdGF agonist or a cdGF antagonist, in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of the biological activities of naturally occurring forms of the cdGF protein. For instance, cdGF homologs can be generated which interfere with the ability of the wild-type protein in forming complexes with either the erbB2 or erbB4 receptor proteins, but which do not substantially interfere with the formation of complexes between the cdGF polypeptide and other members of the erbB receptor family, such as may be involved in other signal transduction mechanisms.

Homologs of the subject cdGF protein can be generated by mutagenesis, such as by discrete point mutation(s), or by truncation. For instance, mutation can give rise to homologs which retain substantially the same, or merely a subset, of the biological activity of the cdGF polypeptide from which it was derived. Alternatively, antagonistic forms of the protein can be generated which are able to inhibit the function of the naturally occurring form of the protein, such as by competitively binding to an erbB receptor.

A protein has cdGF polypeptide biological activity if it has one or more of the following properties: the ability to modulate proliferation, survival and/or differentiation of a cell which expresses an erbB receptor, such as a erbB2 or erbB4 receptor; the ability to modulate proliferation, survival and/or differentiation of mesodermally-derived tissue, such as tissue derived from dorsal mesoderm; the ability to modulate proliferation, survival and/or differentiation of ectodermally-derived tissue, such as tissue derived from the neural tube, neural crest, or head mesenchyme; the ability to modulate proliferation, survival and/or differentiation of endodermally-derived tissue, such as tissue derived from the primitive gut. In general, the ability to bind an erbB receptor protein, e.g. erbB2 and/or erbB4, is sufficient to be characterized as having the biochemical activity of a cdGF polypeptide of the present invention. Thus, according to the present invention, a polypeptide has biological activity if it is a specific agonist or antagonist of a naturally-occurring form of a cdGF protein.

Preferred nucleic acids encode a cdGF polypeptide comprising an amino acid sequence at least 75% homologous, more preferably 80% homologous and most preferably 85% homologous with an amino acid sequence shown in one of SEQ ID No: 2 or 4. Nucleic acids which encode polypeptides having an activity of a cdGF polypeptide and having an amino acid sequence at least about 90%, more preferably at least about 95%, and most preferably at least about 98–99% homology with a sequence shown in one of SEQ ID No: 2 or 4 are also within the scope of the invention. In one embodiment, the nucleic acid is a cDNA encoding a peptide having at least one activity of the subject cdGF polypeptide. Preferably, the nucleic acid is a cDNA molecule comprising at least a portion of the nucleotide sequence represented in SEQ ID No: 1 or 3. A preferred portion of this cDNA molecules includes the coding region of the gene.

Another aspect of the invention provides a nucleic acid which hybridizes under high or low stringency conditions to a nucleic acid which encodes a peptide having all or a portion of an amino acid sequence shown in SEQ ID No: 2 or 4. Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

Nucleic acids, having a sequence that differs from the nucleotide sequence shown in SEQ ID No: 1 or 3 due to degeneracy in the genetic code are also within the scope of the invention. Such nucleic acids encode functionally equivalent peptides (i.e., a peptide having a biological activity of a cdGF polypeptide) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of the cdGF polypeptide. However, it is expected that DNA sequence polymorphisms that do lead to changes in the amino acid sequences of the subject cdGF polypeptides will exist among vertebrates. One skilled in the art will appreciate that these variations in one or more nucleotides (up to about 3–5% of the nucleotides) of the nucleic acids encoding polypeptides having an activity of a cdGF polypeptide may exist among individuals of a given species due to natural allelic variation. Any and all such nucleotide variations and resulting amino acid polymorphisms are within the scope of this invention.

Fragments of the nucleic acids encoding an active portion of the cdGF protein are also within the scope of the invention. As used herein, a fragment of the nucleic acid encoding the active portion of a cdGF polypeptide refers to a nucleic acid having fewer nucleotides than the nucleotide sequence encoding the entire amino acid sequence of the cdGF protein represented in SEQ ID No: 2 or 4, but which nevertheless encodes a peptide having a cdGF polypeptide biological activity, e.g. the fragment retains the ability to bind to an erbB receptor. For instance, cdGF-1 polypeptides can be provided which lack an endogenous signal sequence or a transmembrane/cytoplasmic domain. Nucleic acid fragments within the scope of the present invention include those capable of hybridizing under high or low stringency conditions with nucleic acids from other species for use in screening protocols to detect cdGF homologs, as well as those capable of hybridizing with nucleic acids from human specimens for use in detecting the presence of a nucleic acid encoding the subject cdGF protein, including alternate isoforms, e.g. mRNA splicing variants. Nucleic acids within the scope of the invention may also contain linker sequences, modified restriction endonuclease sites and other sequences useful for molecular cloning, expression or purification of recombinant forms of the subject cdGF polypeptides.

As indicated by the examples set out below, a nucleic acid encoding a peptide having an activity of a cdGF polypeptide may be obtained from mRNA present in any of a number of eukaryotic cells. It should also be possible to obtain nucleic acids encoding cdGF polypeptides of the present invention from genomic DNA obtained from both adults and embryos. For example, a gene encoding a cdGF protein can be cloned from either a cDNA or a genomic library in accordance with protocols described herein, as well as those generally known to persons skilled in the art. A cDNA encoding a cdGF protein can be obtained by isolating total mRNA from a cell, e.g. a mammalian cell, e.g. a human cell, including embryonic cells. Double stranded cDNAs can then be prepared from the total mRNA, and subsequently inserted into a suitable plasmid or bacteriophage vector using any one of a number of known techniques. The gene encoding the cdGF protein can also be cloned using established polymerase chain reaction techniques in accordance with the nucleotide sequence information provided by the invention. The nucleic acid of the invention can be DNA or RNA. A preferred nucleic acid is a cDNA represented by a nucleotide sequence shown in SEQ ID No: 1 or 3.

Another aspect of the invention relates to the use of the isolated nucleic acid in "antisense" therapy. As used herein, "antisense" therapy refers to administration or in situ generation of oligonucleotide probes or their derivatives which specifically hybridizes (e.g. binds) under cellular conditions, with the cellular mRNA and/or genomic DNA encoding a cdGF protein so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a cdGF protein. Alternatively, the antisense construct is an oligonucleotide probe which is generated ex vivo and which, when introduced into the cell causes inhibition of expression by hybridizing with the mRNA and/or genomic sequences of am cdGF gene. Such oligonucleotide probes are preferably modified oligonucleotide which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by van der krol et al. (1988) *Biotechniques* 6: 958–976; and Stein et al. (1988) *Cancer Res* 48: 2659–2668.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of loads of administration, including systemic and topical or localized administration. Techniques and formulations generally may be found in *Remmington's Pharmaceutical Sciences*, Meade Publishing Co., Easton, Pa. For systemic administration, injection is preferred, including intramuscular, intravenous, intraperitoneal, and subcutaneuos for injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as generally known in the art.

In addition to use in therapy, the oligomers of the invention may be used as diagnostic reagents to detect the presence or absence of the target DNA or RNA sequences to which they specifically bind. Such diagnostic tests are described in further detail below.

Likewise, the antisense constructs of the present invention, by antagonizing the normal biological activity of cdGF, can be used in the manipulation of tissue, e.g. tissue differentiation, both in vivo and in ex vivo tissue cultures.

This invention also provides expression vectors containing a nucleic acid encoding a cdGF polypeptide, operably linked to at least one transcriptional regulatory sequence. Operably linked is intended to mean that the nucleotide sequence is linked to a regulatory sequence in a manner which allows expression of the nucleotide sequence. Regulatory sequences are art-recognized and are selected to direct expression of the subject cdGF proteins. Accordingly, the term transcriptional regulatory sequence includes promoters, enhancers and other expression control elements. Such regulatory sequences are described in Goeddel; *Gene Expression Technology: Methods in Enzymology* 185, Academic Press, San Diego, Calif. (1990). For instance, any of a wide variety of expression control sequences-sequences that control the expression of a DNA sequence when operatively linked to it may be used in these vectors to express DNA sequences encoding the cdGF polypeptides of this invention. Such useful expression control sequences, include, for example, a viral LTR, such as the LTR of the Moloney murine leukemia virus, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage λ, the control regions for fd coat protein, the promoter for 3-phosphoglycerate kinase or other glycolytic enzymes, the promoters of acid phosphatase, e.g., Pho5, the promoters of the yeast a-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered. In one embodiment, the expression vector includes a recombinant gene encoding a peptide having an agonistic activity of a subject cdGF polypeptide, or alternatively, encoding a peptide which is an antagonistic form of the cdGF protein. Such expression vectors can be used to transfect cells and thereby produce proteins or peptides, including fusion proteins or peptides, encoded by nucleic acids as described herein.

Moreover, the gene constructs of the present invention can also be used as a part of a gene therapy protocol to deliver nucleic acids encoding either an agonistic or antagonistic form of the subject cdGF protein. Thus, another aspect of the invention features expression vectors for in vivo transfection and expression of a cdGF polypeptide in particular cell types so as to reconstitute the function of, or alternatively, abrogate the function of cdGF in a tissue in which cdGF is misexpressed; or to deliver a form of the protein which alters differentiation of tissue, or which inhibits neoplastic transformation, by modulating the biological function of an erbB receptor.

Expression constructs of the subject cdGF polypeptide, and mutants thereof, may be administered in any biologically effective carrier, e.g. any formulation or composition capable of effectively delivering the cdGF gene to cells in vivo. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically. Furthermore, it will be recognized that the particular gene construct provided for in vivo transduction of cdGF expression are also useful for in vitro transduction of cells, such as for use in the ex vivo tissue culture systems described below.

A preferred approach for in vivo introduction of nucleic acid into a cell is by use of a viral vector containing nucleic acid, e.g. a cDNA, encoding the particular form of the cdGF polypeptide desired. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76: 271). Thus, recombinant retrovirus can be constructed in which part of the retroviral coding sequence (gag, pol, env) has been replaced by nucleic acid encoding one of the subject receptors rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ΨCrip, ΨCre, Ψ2 and ΨAm. Retroviruses have been used to introduce a variety of genes into many different cell types, including neuronal cells, in vitro and/or in vivo (see for example Eglitis, et al. (1985) *Science* 230: 1395–1398; Danos and Mulligan (1988) *Proc. Natl. Acad. Sci. USA* 85: 6460–6464; Wilson et al. (1988) *Proc. Natl. Acad. Sci. USA* 85: 3014–3018; Armentano et al. (1990) *Proc. Natl. Acad. Sci. USA* 87: 6141–6145; Huber et al. (1991) *Proc. Natl. Acad. Sci. USA* 88: 8039–8043; Ferry et al. (1991) *Proc. Natl. Acad. Sci. USA* 88: 8377–8381; Chowdhury et al. (1991) *Science* 254: 1802–1805; van Beusechem et al. (1992) *Proc. Natl. Acad. Sci. USA* 89: 7640–7644; Kay et al. (1992) *Human Gene Therapy* 3: 641–647; Dai et al. (1992) *Proc. Natl. Acad Sci. USA* 89: 10892–10895; Hwu et al. (1993) *J. Immunol.* 150: 4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al. (1989) *PNAS* 86: 9079–9083; Julan et al. (1992) *J Gen Virol* 73: 3251–3255; and Goud et al. (1983) *Virology* 163: 251–254); or coupling cell surface receptor ligands to the viral env proteins (Neda et al. (1991) *J Biol Chem* 266: 14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector in to an amphotropic vector.

Moreover, use of retroviral gene delivery can be further enhanced by the use of tissue- or cell-specific transcriptional regulatory sequences which control expression of the cdGF gene of the retroviral vector.

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See for example Berkner et al. (1988) *BioTechniques* 6: 616; Rosenfeld et al. (1991) *Science* 252: 431-434; and Rosenfeld et al. (1992) *Cell* 68: 143–155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J Virol.* 57: 267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) *Cell* 16: 683; Berkner et al., supra; and Graham et al. in *Methods in Molecular Biology*, E. J. Murray, Ed. (Humana, Clifton, N.J., 1991) vol. 7. pp. 109–127). Expression of the inserted cdGF gene can be under control of, for example, the E1A promoter, the major late promoter (MLP) and associated leader sequences, the E3 promoter, or exogenously added promoter sequences.

Yet another viral vector system useful for delivery of the subject cdGF gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158: 97–129). It is also one of the few viruses that may integrate its DNA into non-dividing cells, and exhibits a high frequency of stable integration (see for example Flotte et al. (1992) *Am. J. Respir. Cell. Mol. Biol.* 7: 349–356; Samulski et al. (1989) *J. Virol.* 63: 3822–3828; and McLaughlin et al. (1989) *J. Virol.* 62: 1963-1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5: 3251–3260 can be used to introduce DNA into cells. A variety of nucleic acids have been introduced into different cell types using AAV vectors (see for example Hermonat et al. (1984) *Proc. Natl. Acad. Sci. USA* 81: 6466–6470; Tratschin et al. (1985) *Mol. Cell. Biol.* 4: 2072–2081; Wondisford et al. (1988) *Mol. Endocrinol.* 2: 32–39; Tratschin et al. (1984) *J Virol.* 51: 611–619; and Flotte et al. (1993) *J. Biol. Chem.* 268: 3781–3790).

In addition to viral transfer methods, such as those illustrated above, non-viral methods can also be employed to cause expression of a cdGF polypeptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject cdGF polypeptide gene by the targeted cell. Exemplary gene delivery systems of this type include liposomal derived systems, poly-lysine conjugates, and artificial viral envelopes.

In a representative embodiment, a gene encoding one of the subject cdGF polypeptides can be entrapped in liposomes bearing positive charges on their surface (e.g., lipofectins) and (optionally) which are tagged with antibodies against cell surface antigens of the target tissue (Mizuno et al. (1992) No Shinkei Geka 20: 547–551; PCT publication WO91/06309; Japanese patent application 1047381; and European patent publication EP-A-43075). For example, lipofection of cells can be carried out using liposomes tagged with monoclonal antibodies against any cell surface antigen present on the tumor cells, as for example, the CD20 antigen which has been detected on the lymphoblastic cell line LK63/CD20+ which also expresses the hek receptor (Wicks et al. (1992) PNAS 89: 1611–1615).

In clinical settings, the gene delivery systems for the therapeutic cdGF gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91: 3054–3057).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

Another aspect of the present invention concerns recombinant forms of the subject cdGF protein which are encoded by genes derived from eukaryotic organisms such as mammals, e.g. humans. Recombinant proteins preferred by the present invention, in addition to native cdGF polypeptides, are at least 75% homologous, more preferably at least 80% homologous and most preferably at least 85% homologous with an amino acid sequence shown in either or both of SEQ ID No: 2 or 4. Polypeptides having an activity of the subject cdGF polypeptides (i.e. either agonistic or antagonistic) and having at least about 90%, more preferably at least about 95%, and most preferably at least about 98–99% homology with a polypeptide sequence in SEQ ID No: 2 or 4 are also within the scope of the invention.

The term "recombinant protein" refers to a polypeptide of the present invention which is produced by recombinant DNA techniques, wherein generally DNA encoding a cdGF polypeptide is inserted into a suitable expression vector which is in turn used to transform a host cell to produce the heterologous protein. Moreover, the phrase "derived from", with respect to a recombinant cdGF gene, is meant to include within the meaning of "recombinant protein" those proteins having an amino acid sequence of a native cdGF polypeptide, or an amino acid sequence similar thereto which is generated by mutations including substitutions and deletions (including truncation) of a naturally occurring form of a cdGF protein. For instance, N-glycosylation sites in the cdGF protein can be modified (e.g. mutated) to preclude glycosylation, allowing expression of a more homogenous, reduced carbohydrate analog in mammalian, insect and yeast expression systems.

Likewise, cdGF polypeptides can be generated which lack an endogenous signal sequence (though this is typically cleaved off even if present in the pro-form of the protein), or which lack a transmembrane domain/cytoplasmic domain. In the instance of the latter, the removal of the C-terminus may result in a soluble form of the protein. In particular, N-terminal fragments of the cdGF-1 polypeptides which are truncated at or before Leu317 are preferred as soluble forms of the protein.

The present invention further pertains to recombinant forms of the subject cdGF polypeptides which are encoded by genes derived from a vertebrate organism, particularly a mammal (e.g. a human), and which have amino acid sequences evolutionarily related to the cdGF proteins represented in SEQ ID No: 2 or 4. Such recombinant cdGF polypeptides are preferably capable of functioning in one of either role of an agonist or antagonist of at least one biochemical/biological activity of the cdGF polypeptide of the appended sequence listing. The term "evolutionarily related to", with respect to amino acid sequences of the present recombinant cdGF polypeptides, refers to cdGF polypeptides having amino acid sequences which have arisen naturally, and also to mutational variants of cdGF polypeptides which are derived, for example, by combinatorial mutagenesis. Such evolutionarily derived cdGF polypeptides preferred by the present invention are at least 70% homologous, more preferably at least 80% homologous and most preferably at least 85% homologous with an amino acid sequence shown in SEQ ID No: 2, 4 and/or 5. Polypeptides having at least about 90%, more preferably at least about 95%, and most preferably at least about 98–99% homology with a sequence shown in SEQ ID No: 2, 4 or 5 are also within the scope of the invention.

The present invention further pertains to methods of producing the subject cdGF polypeptides. For example, a host cell transfected with a nucleic acid vector directing expression of a nucleotide sequence encoding the subject cdGF polypeptide can be cultured under appropriate conditions to allow expression of the peptide to occur. The peptide may be secreted and isolated from a mixture of cells and medium containing the recombinant cdGF polypeptide. Alternatively, the peptide may be retained cytoplasmically by removing the signal peptide sequence from the recombinant cdGF gene and the cells harvested, lysed and the protein isolated. A cell culture includes host cells, media and other byproducts. Suitable media for cell culture are well known in the art. The recombinant cdGF polypeptide peptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant cdGF polypeptide is a fusion protein containing a domain which facilitates its purification, such as a cdGF/GST fusion protein or a poly(His) tagged cdGF protein.

This invention also pertains to a host cell transfected to express a recombinant form of the subject cdGF polypeptides. The host cell may be any prokaryotic or eukaryotic cell, and the choice can be based at least in part on the desirability of such post-translation modifications as glycosylation. Thus, a nucleotide sequence derived from the cloning of cdGF, encoding all or a selected portion of the full-length protein, can be used to produce a recombinant form of a cdGF polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. EGF, interferons, heregulins, neu differentiation factor and the like. Similar procedures, or modifications thereof, can be employed to prepare recombinant cdGF polypeptides by microbial means or tissue-culture technology in accord with the subject invention.

The recombinant cdGF gene can be produced by ligating nucleic acid encoding the subject cdGF protein, or a portion thereof, into a vector suitable for expression in either prokaryotic cells, eukaryotic cells, or both. Expression vectors for production of recombinant forms of the subject cdGF polypeptides include plasmids and other vectors. For instance, suitable vectors for the expression of a cdGF polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli.*

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in *Experimental Manipulation of Gene Expression*, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used. In an illustrative embodiment, a cdGF polypeptide is produced recombinantly utilizing an expression vector generated by sub-cloning the coding sequence of a cdGF gene represented in SEQ ID NO. 1, 3 or 5.

The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual,* 2nd Ed., ed. by Sambrook, Fritsch and Maniatis (Cold Spring Harbor Laboratory Press: 1989) Chapters 16 and 17. In some instances, it may be desirable to express the recombinant cdGF polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When it is desirable to express only a portion of a cdGF protein, such as a form lacking a portion of the N-terminus, i.e. a trunction mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) *J. Bacteriol.* 169: 751–757) and *Salmonella typhimurium* and its in vitro activity has been demonstrated on recombinant proteins (Miller et al. (1987) *PNAS* 84: 2718–1722). Therefore, removal of an N-terminal methionine, if desired, can be achieved either in vivo by expressing cdGF-derived polypeptides in a host which produces MAP (e.g., *E. coli* or CM89 or *S. cerevisiae*), or in vitro by use of purified MAP (e.g., procedure of Miller et al., supra).

Alternatively, the coding sequences for the polypeptide can be incorporated as a part of a fusion gene including a nucleotide sequence encoding a different polypeptide. This type of expression system can be useful under conditions where it is desirable to produce an immunogenic fragment of a cdGF protein. For example, the VP6 capsid protein of rotavirus can be used as an immunologic carrier protein for portions of the cdGF polypeptide, either in the monomeric form or in the form of a viral particle. The nucleic acid sequences corresponding to the portion of a subject cdGF protein to which antibodies are to be raised can be incorporated into a fusion gene construct which includes coding sequences for a late vaccinia virus structural protein to produce a set of recombinant viruses expressing fusion proteins comprising cdGF epitopes as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of a cdGF protein and the poliovirus capsid protein can be created to enhance immunogenicity of the set of polypeptide antigens (see, for example, EP Publication No: 0259149; and Evans et al. (1989) *Nature* 339: 385; Huang et al. (1988) *J Virol.* 62: 3855; and Schlienger et al. (1992) *J. Virol.* 66: 2).

The Multiple Antigen Peptide system for peptide-based immunization can also be utilized to generate an immunogen, wherein a desired portion of a cdGF polypeptide is obtained directly from organo-chemical synthesis of the peptide onto an oligomeric branching lysine core (see, for example, Posnett et al. (1988) *JBC* 263: 1719 and Nardelli et al. (1992) *J. Immunol.* 148: 914). Antigenic determinants of cdGF proteins can also be expressed and presented by bacterial cells.

In addition to utilizing fusion proteins to enhance immunogenicity, it is widely appreciated that fusion proteins can also facilitate the expression of proteins, including the cdGF polypeptides of the present invention. For example, a cdGF polypeptide can be generated as a glutathione-S-transferase (GST-fusion protein). Such GST-fusion proteins can enable easy purification of the cdGF polypeptide, as for example by the use of glutathione-derivatized matrices (see, for example, *Current Protocols in Molecular Biology*, eds. Ausubel et al. (N.Y.: John Wiley & Sons, 1991)). In another embodiment, a fusion gene coding for a purification leader sequence, such as a poly-(His)/enterokinase cleavage site sequence, can be used to replace the signal sequence which naturally occurs at N-terminus the cdGF protein, in order to permit purification of the poly(His)-cdGF protein by affinity chromatography using a $Ni^{2+}$ metal resin. The purification leader sequence can then be subsequently removed by treatment with enterokinase (e.g., see Hochuli et al. (1987) *J. Chromatography* 411: 177; and Janknecht et al. *PNAS* 88: 8972).

Furthermore, the generation of cdGF fusion proteins can be utilized as means for facilitating clustering, e.g., oligomerization, of cdGF proteins to enhance certain activities associated with, for example, receptor cross-linking. For example, a cdGF/alkaline phosphatase fusion protein may provide such a function, relying on the ability of alkaline phosphatase domains to promote complex formation between two or more cdGF/AP proteins. Moreover, it may be desirable to provide multiple cdGF domains in the same molecule, rather than rely on intermolecular complementation for oligomerization. For instance, an unstructured polypeptide linker region can be introduced between two cdGF portions of the fusion protein. This linker can facilitate enhanced flexibility of the fusion protein, allowing the cdGF domains to freely interact through intramolecular association, e.g., because of reduced steric hindrance between the two fragments, as well as permit appropriate folding of each fragment to occur. The linker can be of natural origin, such as a sequence determined to exist in random coil between two domains of a protein. Alternatively, the linker can be of synthetic origin. For instance, the sequence $(Gly_4Ser)_3$ can be used as a synthetic unstructured linker. Linkers of this type are described in Huston et al. (1988) *PNAS* 85: 4879; and U.S. Pat. No. 5,091,513, both incorporated by reference herein.

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al. John Wiley & Sons: 1992).

The cdGF polypeptide may also be chemically modified to create cdGF derivatives by forming covalent or aggregative conjugates with other chemical moieties, such as glycosyl groups, lipids, phosphate, acetyl groups and the like. Covalent derivatives of cdGF can be prepared by linking the chemical moeities to functional groups on cdGF amino acid sidechains or at the N-terminus or at the C-terminus of the polypeptide. For instance, a cdGF protein can generated which includes a moiety, other than sequences naturally associated with the cdGF protein, that binds a component of the extracellular matrix and enhances localization of the cdGF analog to cell surfaces. For example, sequences derived from the fibronectin "type-III repeat", such as a tetrapeptide sequence R-G-D-S (Pierschbacher et al. (1984) *Nature* 309: 30–3; and Komblihtt et al. (1985) *EMBO* 4: 1755–9) can be added to the cdGF polypepyide to support attachment of the chimeric molecule to a cell through binding ECM components (Ruoslahti et al. (1987) *Science* 238: 491–497; Pierschbacheret al. (1987) *J. Biol. Chem.* 262: 17294–8.; Hynes (1987) *Cell* 48: 549–54; and Hynes (1992) *Cell* 69: 11–25) particularly where the cdGF polypeptide lacks the C-terminal transmembrane and cytoplasmic domains.

The present invention also makes available isolated cdGF polypeptides which are isolated from, or otherwise substantially free of other cellular and extracellular proteins, especially erbB receptor proteins or other extracellular factors, normally associated with the cdGF polypeptide. The term "substantially free of other cellular or extracellular proteins" (also referred to herein as "contaminating proteins") or "substantially pure or purified preparations" are defined as encompassing preparations of cdGF polypeptides having less than 20% (by dry weight) contaminating protein, and preferably having less than 5% contaminating protein. Functional forms of the subject cdGF polypeptides can be prepared, for the first time, as purified preparations by using a cloned gene as described herein. Alternatively, the subject cdGF polypeptides can be isolated by affinity purification using, for example, matrix bound erbB receptor protein. By "purified", it is meant, when referring to a peptide or DNA or RNA sequence, that the indicated molecule is present in the substantial absence of other biological macromolecules, such as other proteins. The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions.

As described above for recombinant polypeptides, isolated cdGF polypeptides can include all or a portion of an amino acid sequence represented in SEQ ID No. 2, 4 or 5, or homologous sequence thereto. Exemplary derivatives of that sequence include proteins which lack glycosylation sites (e.g. to produce an unglycosylated protein), or which lack an N-terminus and or/C-terminus sequence, e.g. a cdGF polypeptide which consists essentially of (with respect to receptor binding) an EGF-like domain.

Furthermore, isolated peptidyl portions of cdGF proteins can also be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a cdGF polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a cdGF polypeptide activity, such as by in vivo competition assays or in vitro protein binding assays with erbB receptors.

It will also be possible to modify the structure of the subject cdGF polypeptides for such purposes as enhancing therapeutic or prophylactic efficacy, or stability (e.g., ex vivo shelf life and resistance to proteolytic degradation in vivo). Such modified peptides, when designed to retain at least one activity of the naturally-occurring form of the protein, are considered functional equivalents of the cdGF polypeptide described in more detail herein. Such modified peptide can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, *Biochemistry*, 2nd ed., Ed. by L. Stryer, W. H. Freeman and Co.: 1981). Whether a change in the amino acid sequence of a peptide results in a functional cdGF homolog (e.g. functional in the sense that it acts to mimic or antagonize the wild-type form) can be readily determined by assessing the ability of the variant peptide to produce a response in cells in a fashion similar to the wild-type cdGF protein or competitively inhibit such a response. Peptides in which more than one replacement has taken place can readily be tested in the same manner.

Accordingly, the present invention contemplates a method of generating sets of combinatorial mutants of the presently disclosed novel cdGF polypeptides, as well as truncation and fragmentation mutants, and is especially useful for identifying potential variant sequences which are functional in binding to an erbB receptor. One purpose for screening such combinatorial libraries is, for example, to isolate novel cdGF homologs which function as one of either an agonist or antagonist of the biological activities of the wild-type ("authentic") protein, or alternatively, which possess novel activities all together. To illustrate, cdGF homologs can be engineered by the present method to provide proteins which bind an erbB receptor yet which block (antagonize) receptor-mediated gene transcription resulting from signal transduction pathways normally associated with activation of that receptor. Such proteins, when expressed from recombinant DNA constructs, can be used in gene therapy protocols, or can be formulated as pharmaceutical preparations and delivered in such manner.

Likewise, mutagenesis can give rise to cdGF homologs which have extracellular half-lives dramatically different than the corresponding wild-type protein. For example, the altered protein can be rendered either more stable or less stable to proteolytic degradation or other extracellular process which result in destruction of, or otherwise inactivation of, a cdGF polypeptide. Such cdGF homologs can be utilized to alter the envelope of bioavailability for a recombinant cdGF protein by modulating, for example, the plasma half-life of the protein. For instance, a short half-life can give rise to more transient biological effects associated with a particular recombinant cdGF polypeptide and can therefore allow tighter control of protein levels within or around a particular tissue. As above, such proteins, and particularly their recombinant nucleic acid constructs, can be used in gene therapy protocols as well as formulated into pharmaceutical preparations.

In an illustrative embodiment of this method, the amino acid sequences for a population of cdGF homologs or other related proteins are aligned, preferably to promote the highest homology possible. Such a population of variants can include, for example, cdGF homologs from one or more species, e.g. various mammals, or cdGF homologs from the same species but which differ due to mutation. Amino acids which appear at each position of the aligned sequences are selected to create a degenerate set of combinatorial sequences. In a preferred embodiment, the variegated library of cdGF variants is generated by combinatorial mutagenesis at the nucleic acid level, and is encoded by a variegated gene library. For instance, a mixture of synthetic oligonucleotides can be enzymatically ligated into gene sequences such that the degenerate set of potential cdGF sequences are expressible as individual polypeptides, or alternatively, as a set of larger fusion proteins (e.g. for phage display) containing the set of cdGF sequences therein.

There are many ways by which the library of potential cdGF homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential cdGF sequences. The synthesis of degenerate oligonucleotides is well known in the art (see for example, Narang, SA (1983) *Tetrahedron* 39: 3; Itakura et al. (1981) *Recombinant DNA, Proc 3rd Cleveland Sympos. Macromolecules*, ed. AG Walton, Amsterdam: Elsevier pp273–289; Itakura et al. (1984) *Annu. Rev. Biochem.* 53: 323; Itakura et al. (1984) *Science* 198: 1056; Ike et al. (1983) *Nucleic Acid Res.* 11: 477. Such techniques have been employed in the directed evolution of other proteins (see, for example, Scott et al. (1990) *Science* 249: 386–390; Roberts et al. (1992) *PNAS* 89: 2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Alternatives to the above combinatorial mutagenesis also exist. For example, cdGF homologs (both agonist and antagonist forms) can be generated and isolated from a library by screening using, for example, alanine scanning mutagenesis and the like (Ruf et al. (1994) *Biochemistry* 33: 1565–1572; Wang et al. (1994) *J. Biol. Chem.* 269: 3095–3099; Balint et al. (1993) *Gene* 137: 109–118; Grodberg et al. (1993) *Eur. J. Biochem.* 218: 597–601; Nagashima et al. (1993) *J. Biol. Chem.* 268: 2888–2892; Lowman et al. (1991) *Biochemistry* 30: 10832–10838; and Cunningham et al. (1989) *Science* 244: 1081–1085), by linker scanning mutagenesis (Gustin et al. (1993) *Virology* 193: 653–660; Brown et al. (1992) *Mol. Cell Biol.* 12: 2644–2652; McKnight et al. (1982) *Science* 232: 316); by saturation mutagenesis (Meyers et al. (1986) *Science* 232: 613); by PCR mutagenesis (Leung et al. (1989) *Method Cell Mol Biol* 1: 11–19); or by random mutagenesis (Miller et al. (1992) *A Short Course in Bacterial Genetics*, CSHL Press, Cold Spring Harbor, N.Y.; and Greener et al. (1994) *Strategies in Mol Biol* 7: 32–34).

A wide range of techniques are known in the art for screening gene products of combinatorial libraries, and for screening cDNA libraries for gene products having a certain property. Such techniques will be generally adaptable for rapid screening of the gene libraries generated by the combinatorial mutagenesis of cdGF homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate cdGF sequences created by combinatorial mutagenesis techniques.

In one screening assay, the candidate cdGF polypeptides are displayed on the surface of a cell or viral particle, and the ability of particular cells or viral particles to bind an erhB receptor protein via this gene product is detected in a "panning assay". For instance, the gene library can be cloned into the gene for a surface membrane protein of a bacterial cell, and the resulting fusion protein detected by panning (Ladner et al., WO 88/06630; Fuchs et al. (1991) *Bio/Technology* 9: 1370–1371; and Goward et al. (1992) *TIBS* 18: 136–140). In a similar fashion, a detectably labeled erbB receptor can be used to score for potentially functional cdGF polypeptide homologs. For example, the Alkaline Phosphatase-erbB2 or Ap-erbB4 fusion proteins, or the equivalent fluorescently labeled receptors, can be used to detect cdGF homologs which retain receptor-binding activity. In the application of fluorescently labeled receptor, cells can be visually inspected and separated under a fluorescence microscope, or, where the morphology of the cell permits, separated by a fluorescence-activated cell sorter.

In an alternate embodiment, the gene library is expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filamentous phages M13, fd., and fl are most often used in phage display libraries, as either of the phage gII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) *J. Biol. Chem.* 267: 16007–16010; Griffiths et al. (1993) *EMBO J* 12: 725–734; Clarkson et al. (1991) *Nature* 352: 624–628; and Barbas et al. (1992) *PNAS* 89: 4457–4461).

In an illustrative embodiment, the recombinant phage antibody system (RPAS, Pharamacia Catalog number 27-9400-01) can be easily modified for use in expressing and screening cdGF combinatorial libraries. For instance, the pCANTAB 5 phagemid of the RPAS kit contains the gene which encodes the phage gIII coat protein. The cdGF combinatorial gene library can be cloned into the phagemid adjacent to the gIII signal sequence such that it will be expressed as a gIII fusion protein. After ligation, the phagemid is used to transform competent *E. coli* TG1 cells. Transformed cells are subsequently infected with M13KO7 helper phage to rescue the phagemid and its candidate cdGF gene insert. The resulting recombinant phage contain phagemid DNA encoding a specific candidate cdGF, and display one or more copies of the corresponding fusion coat protein. The phage-displayed candidate cdGF proteins which are capable of binding a cdGF receptor are selected or enriched by panning. For instance, the phage library can be on glutathione-immobilized erbB receptor/GST fusion proteins to enrich for cdGF homologs which retain an ability to bind an erbB receptor. The bound phage is then isolated, and if the recombinant phage express at least one copy of the wild type gIII coat protein, they will retain their ability to infect *E. coli*. Thus, successive rounds of reinfection of *E. coli*, and panning will greatly enrich for cdGF homologs.

Each of these homologs can subsequently be screened for further biological activities in order to differentiate agonists and antagonists. For example, receptor-binding homologs isolated from the combinatorial library can be tested for their effect on cellular proliferation relative to the wild-type form of the protein. Alternatively, one could screen the homologs for agonists by detecting autophosphorylation of an erbB receptor in response to treatment with the homolog (see, for example, Millauer et al. (1993) *Cell* 72: 835–846). In similar fashion, antagonists can be identified from the enriched fraction based on their ability to inhibit autophosphorylation of the receptor by wild-type cdGF protein.

In another embodiment, the combinatorial library is designed to be extracellularly presented (e.g. as it occurs naturally) and, though optionally, secreted (e.g. the polypeptides of the library all include a signal sequence but no transmembrane or cytoplasmic domains). The gene can be used to transfect a eukaryotic cell that can be co-cultured with cells which express an functional erbB receptor, e.g. a erbB2 or erbB4 receptor, and which are sensitive to treatment with the wild-type soluble form of cdGF. Functional cdGF homologs secreted by the cells expressing the combinatorial library will diffuse to neighboring erbB+ cells and induce a phenotypic change. Using, for example, antibodies directed to epitopes which are either created or destroyed in response to cdGF treatment, the pattern of detection of cdGF induction will resemble a gradient function, and will allow the isolation (generally after several repetitive rounds of selection) of cells producing active cdGF homologs. Likewise, cdGF antagonists can be selected in similar fashion by the ability of the cell producing a functional antagonist to protect neighboring cells from the effect of authentic cdGF added to the culture media.

To illustrate, target cells are cultured in 24-well microtitre plates. The target cells can be, for instance, cells which naturally express erbB2 and/or erbB4 receptors, such as MDA-MB 453 cells, or cells which have been transfected with genes encoding such receptors. COS-7 cells are transfected with the combinatorial cdGF gene library and cultured (optionally) in a cell culture insert (e.g. Collaborative Biomedical Products, Catalog #40446) that are able to fit into the wells of the microtitre plate. The cell culture inserts are placed in the wells such that recombinant cdGF homologs secreted by the cells in the insert can diffuse through the porous bottom of the insert and contact the target cells in the microtitre plate wells. After a period of time sufficient for functional forms of ed GF to produce a measurable response in the target cells, the inserts are removed and the effect of any cdGF homologs on the target cells determined. Cells from the inserts corresponding to wells which score positive for activity can be split and re-cultured on several inserts, the process being repeated until the active clones are identified.

The invention also provides for reduction of the cdGF polypeptides to generate mimetics, e.g. peptide or non-peptide agents, which are able to disrupt binding of a cdGF polypeptide of the present invention with an erbB receptor. Accordingly, such mutagenic techniques as described above are also useful to map the determinants of the cdGF polypeptides which participate in protein-protein interactions involved in, for example, binding of the subject cdGF polypeptide to an erbB receptor or in causing oligomerization of receptors. To illustrate, the critical residues of a subject cdGF polypeptide which are involved in molecular recognition of an erbB receptor can be determined and used to generate cdGF polypeptide-derived peptidomimetics which competitively inhibit binding of the authentic cdGF protein with that receptor. By employing, for example, scanning mutagenesis to map the amino acid residues of the cdGF protein involved in binding the erbB receptor, peptidomimetic compounds can be generated which mimic those residues in binding to the receptor and which consequently can inhibit binding of cdGF to the receptor and interfere with its function.

For instance, non-hydrolyzable peptide analogs of such residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gama lactam rings (Garvey et al. in *Peptides. Chemistry and Biology*, G. R. Marshall ed., ESCOM Publisher: Leiden, Netherlands, 1988), keto-methylene pseudopeptides (Ewenson et al. (1986) *J Med Chem* 29: 295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26: 647; and Sato et al. (1986) *J Chem Soc Perkin Trans* 1: 1231), and β-aminoalcohols (Gordon et al. (1985) *Biochem Biophys Res Commun* 126: 419; and Dann et al. (1986) *Biochem Biophys Res Commun* 134: 71).

Another aspect of the invention pertains to an antibody specifically reactive with a cdGF protein. For example, by using immunogens derived from a cdGF protein, e.g. based on the cDNA sequences, anti-protein/anti-peptide antisera or monoclonal antibodies can be made by standard protocols (See, for example, Antibodies. *A Laboratory Manual* ed. by Harlow and Lane (Cold Spring Harbor Press: 1988)). A mammal, such as a mouse, a hamster or rabbit can be immunized with an immunogenic form of the peptide (e.g., a cdGF polypeptide or an antigenic fragment which is capable of eliciting an antibody response). Techniques for conferring immunogenicity on a protein or peptide include conjugation to carriers or other techniques well known in the art. An immunogenic portion of the cdGF protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of the cdGF protein of the present invention, e.g. antigenic determinants of a protein represented by SEQ ID No: 2 and/or SEQ ID No: 4, or a closely related human or non-human mammalian homolog (e.g. at least 85 percent homologous, preferably at least 90 percent homologous, and more preferably at least 95 percent homologous). In yet a further preferred embodiment of the present invention, the anti-cdGF polypeptide antibodies do not substantially cross react (i.e. does not react specifically) with a protein which is, for example, less than 85 percent homologous to SEQ ID No: 2; e.g. less than 95 percent homologous with one of SEQ ID No: 2; e.g. less than 98–99 percent homologous with one of SEQ ID No: 2; less than 85 percent homologous to SEQ ID No: 4; e.g. less than 95 percent homologous with one of SEQ ID No: 4; e.g. less than 98–99 percent homologous with one of SEQ ID No: 4. By "not substantially cross react", it is meant that the antibody has a binding affinity for a non-homologous protein (e.g. heregulin, NDF, GGF or ARIA proteins) which is at least one order of magnitude, more preferably at least 2 orders of magnitude, and even more preferably at least 3 orders of magnitude less than the binding affinity of the antibody for the protein of SEQ ID No: 2 or SEQ ID No: 4.

Following immunization, anti-cdGF antisera can be obtained and, if desired, polyclonal anti-cdGF antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) *Nature*, 256: 495–497), the human B cell hybridoma technique (Kozbar et al., (1983) *Immunology Today*, 4: 72), and the EBV-hybridoma technique to produce human monoclonal antibodies (Cole et al., (1985) *Monoclonal Antibodies and Cancer Therapy*, Alan R. Liss, Inc. pp. 77–96). Hybridoma cells can be screened immunochemically for production of antibodies specifically reactive with a cdGF polypeptide of the present invention and monoclonal antibodies isolated from a culture comprising such hybridoma cells.

The term antibody as used herein is intended to include fragments thereof which are also specifically reactive with one of the subject cdGF polypeptide. Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragment can be treated to reduce disulfide bridges to produce Fab fragments. The antibody of the present invention is further intended to include single chain, bi-specific and chimeric molecules having a cdGF affinity conferred by at least one CDR region of the antibody.

Both monoclonal and polyclonal antibodies (Ab) directed against cdGF polypeptide or cdGF polypeptide variants, and antibody fragments such as Fab and F(ab)$_2$, can be used to block the action of cdGF and allow the study of the role of cdGF in, for example, embryogenesis and/or tumorogenesis. For example, purified monoclonal Abs can be injected directly into the limb buds of chick or mouse embryos. Thus, the use of anti-cdGF Abs during this developmental stage can allow assessment of the effect of cdGF on the formation of limbs in vivo. In a similar approach, hybridomas producing anti-cdGF monoclonal Abs, or biodegradable gels in which anti-cdGF Abs are suspended, can be implanted at a site proximal or within the area at which cdGF action is intended to be blocked. Experiments of this nature can aid in deciphering the role of this and other factors that may be involved in limb patterning and tissue formation.

Antibodies which specifically bind cdGF polypeptide epitopes can also be used in immunohistochemical staining of tissue samples in order to evaluate the abundance and pattern of expression of each of the subject cdGF polypeptides. Anti-cdGF antibodies can be used diagnostically in immuno-precipitation and immuno-blotting to detect and evaluate cdGF protein levels in tissue or bodily fluid as part of a clinical testing procedure. For instance, such measurements can be useful in predictive valuations of the onset or progression of neurological disorders, such as those marked by denervation-like or disuselike symptoms. Likewise, the ability to monitor cdGF levels in an individual can allow determination of the efficacy of a given treatment regimen for an individual afflicted with such a disorder. The level of cdGF polypeptides can be measured in bodily fluid, such as in samples of cerebral spinal fluid, or can be measured in tissue, such as produced by biopsy. Diagnostic assays using anti-cdGF antibodies can include, for example, immunoassays designed to aid in early diagnosis of a neurodegenerative disorder, particularly ones which are manifest at birth. Diagnostic assays using anti-cdGF polypeptide antibodies can also include immunoassays designed to aid in early diagnosis and phenotyping of a neoplastic or hyperplastic disorder.

Another application of anti-cdGF antibodies of the present invention is in the immunological screening of cDNA libraries constructed in expression vectors such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a cdGF protein can then be detected with antibodies, as, for example, reacting nitrocellulose filters lifted from infected plates with anti-cdGF antibodies. Positive phage detected by this assay can then be isolated from the infected plate. Thus, the presence of cdGF homologs (orthologs) can be detected and cloned from other animals, as can alternate isoforms (including splicing variants).

Moreover, the nucleotide sequence determined from the cloning of the cdGF gene will further allow for the generation of probes and primers designed for use in identifying and/or cloning cdGF homologs in other cell types, e.g. from other tissues, as well as cdGF homologs from other animals, e.g. humans. For instance, the present invention also provides a probe/primer comprising a substantially purified oligonucleotide, which oligonucleotide comprises a region of nucleotide sequence that hybridizes under stringent conditions to at least 10 consecutive nucleotides of sense or anti-sense sequence of SEQ ID No: 1 and/or SEQ ID No: 3, or naturally occurring mutants thereof. For instance, primers based on the nucleic acids represented in SEQ ID No. 1 or 3 can be used in PCR reactions to clone cdGF homologs. Likewise, probes based on the cdGF gene sequences of SEQ ID No. 1 and 3 can be used to detect cdGF transcripts or genomic sequences. In preferred embodiments, the probe further comprises a label group attached thereto and able to be detected, e.g. the label group is selected from the group consisting of radioisotopes, fluorescent compounds, enzymes, and enzyme co-factors. Such probes can also be used as a part of a diagnostic test kit for identifying cells in which cdGF is misexpressed, such as by measuring a level of a cdGF encoding nucleic acid in a sample of cells from a patient; e.g. detecting cdGF mRNA levels or determining whether a genomic cdGF gene has been mutated or deleted.

To illustrate, nucleotide probes can be generated from the cdGF gene which facilitate histological screening of intact tissue and tissue samples for the presence of a cdGF polypeptide mRNA. Similar to the diagnostic uses of anti-cdGF polypeptide antibodies, the use of probes directed to cdGF messages, or to genomic cdGF sequences, can be used for both predictive and therapeutic evaluation of allelic mutations which might be manifest in, for example, neoplastic or hyperplastic disorders (e.g. unwanted cell growth) or abnormal differentiation of tissue. Used in conjunction with anti-cdGF immunoassays, the nucleotide probes can help facilitate the determination of the molecular basis for a developmental disorder which may involve some abnormality associated with expression (or lack thereof) of a cdGF polypeptide. For instance, variation in cdGF polypeptide synthesis can be differentiated from a mutation in the cdGF coding sequence.

Accordingly, the present method provides a method for determining if a subject is at risk for a disorder characterized by unwanted cell proliferation or abherent control of differentiation. In preferred embodiments, the subject method can be generally characterized as comprising detecting, in a tissue sample of the subject (e.g. a human patient), the presence or absence of a genetic lesion characterized by at least one of (i) a mutation of a gene encoding a cdGF polypeptide or (ii) the mis-expression of a cdGF gene. To illustrate, such genetic lesions can be detected by ascertaining the existence of at least one of (i) a deletion of one or more nucleotides from a cdGF gene, (ii) an addition of one or more nucleotides to such a cdGF gene, (iii) a substitution of one or more nucleotides of a cdGF gene, (iv) a gross chromosomal rearrangement of a cdGF genes, (v) a gross alteration in the level of a messenger RNA transcript of a cdGF gene, (vi) the presence of a non-wild type splicing pattern of a messenger RNA transcript of a cdGF gene, and (vii) a non-wild type level of a cdGF polypeptide. In one aspect of the invention there is provided a probe/primer comprising an oligonucleotide containing a region of nucleotide sequence which is capable of hybridizing to a sense or antisense sequence of SEQ ID Nos: 1, 3 and/or 5, or naturally occurring mutants thereof, or 5' or 3' flanking sequences or intronic sequences naturally associated with a cdGF gene. The probe is exposed to nucleic acid of a tissue sample; and the hybridization of the probe to the sample nucleic acid is detected. In certain embodiments, detection of the lesion comprises utilizing the probe/primer in a polymerase chain reaction (PCR) (see, e.g., U.S. Pat. Nos: 4,683,195 and 4,683,202) or, alternatively, in a ligation chain reaction (LCR) (see, e.g., Landegran et al. (1988) *Science*, 241: 1077–1080; and NaKazawa et al. (1944) *PNAS* 91: 360–364) the later of which can be particularly useful for detecting point mutations in the cdGF gene. Alternatively, immunoassays can be employed to determine the level of cdGF protein, either soluble or membrane bound.

Also, the use of anti-sense techniques (e.g. microinjection of antisense molecules, or transfection with plasmids whose transcripts are anti-sense with regard to a cdGF mRNA or gene sequence) can be used to investigate role of cdGF in developmental events, as well as the normal cellular function of cdGF in adult tissue. Such techniques can be utilized in cell culture, but can also be used in the creation of transgenic animals.

Furthermore, by making available purified and recombinant cdGF polypeptides, the present invention facilitates the development of assays which can be used to screen for drugs, or for cdGF homologs, which are either agonists or antagonists of the normal cellular function of the subject cdGF polypeptides, or of their role in the pathogenesis of cellular proliferation and/or differentiation and disorders related thereto. In one embodiment, the assay evaluates the ability of a compound to modulate binding between a cdGF polypeptide and an erbB receptor. A variety of assay formats will suffice and, in light of the present inventions, will be comprehended by skilled artisan.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with receptor proteins. Accordingly, in an exemplary screening assay of the present invention, the compound of interest is contacted with an erbB receptor polypeptide which is ordinarily capable of binding a cdGF protein. To the mixture of the compound and receptor is then added a composition containing a cdGF polypeptide. Detection and quantification of receptor/cdGF complexes provides a means for determining the compound's efficacy at inhibiting (or potentiating) complex formation between the receptor protein and the cdGF polypeptide. The efficacy of the compound can be assessed by generating dose response curves from data obtained using various concentrations of the test compound. Moreover, a control assay can also be performed to provide a baseline for comparison. In the control assay, isolated and purified cdGF polypeptide is added to a composition containing the receptor protein, and the formation of receptor/cdGF complex is quantitated in the absence of the test compound.

Complex formation between the cdGF polypeptide and an erbB receptor may be detected by a variety of techniques. For instance, modulation of the formation of complexes can be quantitated using, for example, detectably labelled proteins such as radiolabelled, fluorescently labelled, or enzymatically labelled cdGF polypeptides, by immunoassay, or by chromatographic detection.

Typically, it will be desirable to immobilize either the erbB receptor or the cdGF polypeptide to facilitate separation of receptor/cdGF complexes from uncomplexed forms of one of the proteins, as well as to accommodate automation of the assay. In one embodiment, a fusion protein can be provided which adds a domain that allows the protein to be bound to a matrix. For example, glutathione-S-transferase/receptor (GST/receptor) fusion proteins can be adsorbed onto glutathione sepharose beads (Sigma Chemical, St. Louis, Mo.) or glutathione derivatized microtitre plates, which are then combined with the cdGF polypeptide, e.g. an $^{35}$S-labeled cdGF polypeptide, and the test compound and incubated under conditions conducive to complex formation, e.g. at physiological conditions for salt and pH, though slightly more stringent conditions may be desired, e.g., at 4° C. in a buffer containing 0.6M NaCl or a detergent such as 0.1% Triton X-100. Following incubation, the beads are washed to remove any unbound cdGF polypeptide, and the matrix bead-bound radiolabel determined directly (e.g. beads placed in scintilant), or in the supernatant after the receptor/cdGF complexes are dissociated. Alternatively, the complexes can dissociated from the bead, separated by SDS-PAGE gel, and the level of cdGF polypeptide found in the bead fraction quantitated from the gel using standard electrophoretic techniques.

Other techniques for immobilizing proteins on matrices are also available for use in the subject assay. For instance, the erbB receptor protein can be immobilized utilizing conjugation of biotin and streptavidin. For instance, biotinylated receptor molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the erbB receptor but which do not interfere with cdGF binding can be derivatized to the wells of the plate, and the receptor trapped in the wells by antibody conjugation. As above, preparations of a cdGF polypeptide and a test compound are incubated in the receptor-presenting wells of the plate, and the amount of receptor/cdGF complex trapped in the well can be quantitated. Exemplary methods for detecting such complexes, in addition to those described above for the GST-immobilized complexes, include immunodetection of complexes using antibodies reactive with the cdGF polypeptide, or which are reactive with the receptor protein and compete for binding with the cdGF polypeptide; as well as enzyme-linked assays which rely on detecting an enzymatic activity associated with the cdGF polypeptide. In the instance of the latter, the enzyme can be chemically conjugated or provided as a fusion protein with the cdGF polypeptide. To illustrate, the cdGF polypeptide can be chemically cross-linked or genetically fused with alkaline phosphatase, and the amount of cdGF polypeptide trapped in the complex can be assessed with a chromogenic substrate of the enzyme, e.g. paranitrophenylphosphate. Likewise, a fusion protein comprising the cdGF polypeptide and glutathione-S-transferase can be provided, and complex formation quantitated by detecting the GST activity using 1-chloro-2,4-dinitrobenzene (Habig et al (1974) *J Biol Chem* 249: 7130).

For processes which rely on immunodetection for quantitating one of the proteins trapped in the complex, antibodies against the protein, such as the anti-cdGF antibodies described herein, can be used. Alternatively, the protein to be detected in the complex can be "epitope tagged" in the form of a fusion protein which includes, in addition to the cdGF polypeptide or erbB receptor sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) *J Biol Chem* 266: 21150–21157) which includes a 10-residue sequence from c-myc, as well as the pFLAG system (International Biotechnologies, Inc.) or the pEZZ-protein A system (Pharamacia, N.J.).

Another aspect of the present invention relates to a method of inducing and/or maintaining a differentiated state, enhancing survival, and/or promoting proliferation of a cell responsive to a cdGF protein, by contacting the cells with a cdGF agonist or a cdGF antagonist. For instance, it is contemplated by the invention that, in light of the present finding of an apparently broad involvement of cdGF proteins in the formation and maintenance of ordered spatial arrangements of differentiated tissues in vertebrates, the subject method could be used to generate and/or maintain an array of different vertebrate tissue both in vitro and in vivo. The cdGF agent can be, as appropriate, any of the preparations described above, including isolated polypeptides, gene therapy constructs, antisense molecules, peptidomimetics or agents identified in the drug assays provided herein.

For example, the present method is applicable to cell culture technique. In vitro neuronal culture systems have proved to be fundamental and indispensable tools for the study of neural development, as well as the identification of neurotrophic factors such as nerve growth factor (NGF), ciliary trophic factors (CNTF), and brain derived neurotrophic factor (BDNF). Once a neuronal cell has become terminally-differentiated it typically will not change to another terminally differentiated cell-type. However, neuronal cells can nevertheless readily lose their differentiated state. This is commonly observed when they are grown in culture from adult tissue, and when they form a blastema during regeneration. The present method provides a means for ensuring an adequately restrictive environment in order to maintain neuronal cells at various stages of differentiation, and can be employed, for instance, in cell cultures designed to test the specific activities of other trophic factors. In such embodiments of the subject method, the cultured cells can be contacted with a cdGF polypeptide, or an agent identified in the assays described above, in order to induce neuronal differentiation (e.g. of a stem cell), or to maintain the integrity of a culture of terminally-differentiated neuronal cells by preventing loss of differentiation. The source of cdGF in the culture can be derived from, for example, a purified or semi-purified protein composition added directly to the cell culture media, or alternatively, released from a polymeric device which supports the growth of various neuronal cells and which has been doped with a cdGF protein. The source of the cdGF can also be a cell that is co-cultured with the intended neuronal cell and which produces either a recombinant or natural form of a cdGF protein. Alternatively, the source can be the neuronal cell itself which as been engineered to produce a recombinant cdGF. In an exemplary embodiment, a naive neuronal cell (e.g. a stem cell) is treated with a cdGF agonist in order to induce differentiation of the cells into, for example, sensory neurons or, alternatively, motorneurons. Such neuronal cultures can be used as convenient assay systems as well as sources of implantable cells for therapeutic treatments. For example, cdGF polypeptides may be useful in establishing and maintaining the olfactory neuron cultures described U.S. Pat. No. 5,318,907 and the like.

To further illustrate potential uses, it is noted that intracerebral grafting has emerged as an additional approach to central nervous system therapies. For example, one approach to repairing damaged brain tissues involves the transplantation of cells from fetal or neonatal animals into the adult brain (Dunnett et al. (1987) *J Exp Biol* 123: 265–289; and Freund et al. (1985) *J Neurosci* 5: 603–616). Fetal neurons from a variety of brain regions can be successfully incorporated into the adult brain, and such grafts can alleviate behavioral defects. For example, movement disorder induced by lesions of dopaminergic projections to the basal ganglia can be prevented by grafts of embryonic dopaminergic neurons. Complex cognitive functions that are impaired after lesions of the neocortex can also be partially restored by grafts of embryonic cortical cells. Thus, use of the present erbB receptor ligands for maintenance of neuronal cell cultures can help to provide a source of implantable neuronal tissue. The use of a cdGF polypeptide in the culture can be to prevent loss of differentiation, or where fetal tissue is used, especially neuronal stem cells, a cdGF polypeptide can be used to induce differentiation.

Stem cells useful in the present invention are generally known. For example, several neural crest cells have been identified, some of which are multipotent and likely represent uncommitted neural crest cells, and others of which can generate only one type of cell, such as sensory neurons, and likely represent committed progenitor cells. The role of a cdGF protein employed in the present method to culture such stem cells can be to induce differentiation of the uncommitted progenitor and thereby give rise to a committed progenitor cell, or to cause further restriction of the developmental fate of a committed progenitor cell towards becoming a terminally-differentiated neuronal cell. For example, the present method can be used in vitro to induce and/or maintain the differentiation of neural crest cells into glial cells, schwann cells, chromaffin cells, cholinergic sympathetic or parasympathetic neurons, as well as peptidergic and serotonergic neurons. The cdGF polypeptide can be used alone, or can be used in combination with other neurotrophic factors which act to more particularly enhance a particular differentiation fate of the neuronal progenitor cell. In the later instance, the cdGF polypeptide might be viewed as ensuring that the treated cell has achieved a particular phenotypic state such that the cell is poised along a certain developmental pathway so as to be properly induced upon contact with a secondary neurotrophic factor. In similar fashion, even relatively undifferentiated stem cells or primative neuroblasts can be maintained in culture and caused to differentiate with treatment of cdGF polypeptides. Exemplary primative cell cultures comprise cells harvested from the neural plate or neural tube of an embryo even before much overt differentiation has occurred.

In addition to the implantation of cells cultured in the presence of a functional cdGF activity, yet another objective of the present invention concerns the therapeutic application of a cdGF polypeptide or mimetic to enhance survival of neurons and other neuronal cells in both the central nervous system and the peripheral nervous system. The ability of cdGF to regulate neuronal differentiation and survival during development of the nervous system and also presumably in the adult state indicates that cdGF can be reasonably expected to facilitate control of adult neurons with regard to maintenance, functional performance, and aging of normal cells; repair and regeneration processes in chemically or mechanically lesioned cells; and prevention of degeneration and premature death which result from loss of differentiation in certain pathological conditions. In light of this understanding, the present invention specifically contemplates applications of the subject proteins to the treatment of (prevention and/or reduction of the severity of) neurological conditions deriving from: (i) acute, subacute, or chronic injury to the nervous system, including traumatic injury, chemical injury, vasal injury and deficits (such as the ischemia resulting from stroke), together with infectious/inflammatory and tumor-induced injury; (ii) aging of the nervous system including Alzheimer's disease; (iii) chronic neurodegenerative diseases of the nervous system, including Parkinson's disease, Huntington's chorea, amylotrophic lateral sclerosis and the like, as well as spinocerebellar degenerations; (iv) chronic immunological diseases of the nervous system or affecting the nervous system, including multiple sclerosis; and (v) disorders of sensory neurons as well as degenerative diseases of the retina.

Many neurological disorders are associated with degeneration of discrete populations of neuronal elements and may be treatable with a therapeutic regimen which includes a cdGF polypeptide (or equivalent thereof). For example, Alzheimer's disease is associated with deficits in several neurotransmitter systems, both those that project to the neocortex and those that reside with the cortex. For instance, the nucleus basalis in patients with Alzheimer's disease were observed to have a profound (75%) loss of neurons compared to age-matched controls. Although Alzheimer's disease is by far the most common form of dementia, several other disorders can produce dementia. Several of these are degenerative diseases characterized by the death of neurons in various parts of the central nervous system, especially the cerebral cortex. However, some forms of dementia are associated with degeneration of the thalmus or the white matter underlying the cerebral cortex. Here, the cognitive dysfunction results from the isolation of cortical areas by the degeneration of efferents and afferents. Huntington's disease involves the degeneration of intrastraital and cortical cholinergic neurons and GABAergic neurons. Pick's disease is a severe neuronal degeneration in the neocortex of the frontal and anterior temporal lobes, sometimes accompanied by death of neurons in the striatum. Treatment of patients suffering from such degenerative conditions can include the application of cdGF polypeptides, or agents which mimic their effects, in order to manipulate, for example, the de-differentiation and apoptosis of neurons which give rise to loss of neurons. In preferred embodiments, a source of a cdGF agent is stereotactically provided within or proximate the area of degeneration.

In addition to degenerative-induced dementias, a pharmaceutical preparation of a cdGF homolog can be applied opportunely in the treatment of neurodegenerative disorders which have manifestations of tremors and involuntary movements. Parkinson's disease, for example, primarily affects subcortical structures and is characterized by degeneration of the nigrostriatal pathway, raphe nuclei, locus cereleus, and the motor nucleus of vagus. Ballism is typically associated with damage to the subthalmic nucleus, often due to acute vascular accident. Also included are neurogenic and myopathic diseases which ultimately affect the somatic division of the peripheral nervous system and are manifest as neuromuscular disorders. Examples include chronic atrophies such as amyotrophic lateral sclerosis, Guillain-Barre syndrome and chronic peripheral neuropathy, as well as other diseases which can be manifest as progressive bulbar palsies or spinal muscular atrophies. The present method is ammenable to the treatment of disorders of the cerebellum which result in hypotonia or ataxia, such as those lesions in the cerebellum which produce disorders in the limbs ipsilateral to the lesion. For instance, a preparation of a cdGF homolog can be used to treat a restricted form of cerebellar corical degeneration involving the anterior lobes (vermis and leg areas) such as is common in alcoholic patients.

In yet another embodiment, the subject method is used to treat amyotrophic lateral sclerosis. ALS is a name given to a complex of disorders that comprise upper and lower motor neurons. Patients may present with progressive spinal muscular atrophy, progressive bulbar palsy, primary lateral sclerosis, or a combination of these conditions. The major pathological abnormality is characterized by a selective and progressive degeneration of the lower motor neurons in the spinal cord and the upper motor neurons in the cerebral cortex. The therapeutic application of a cdGF therapeutic agent, such as a soluble form of a polypeptide represented in either of SEQ ID No: 2, 4 or 6, or a peptidomimetic thereof, can be used alone or in conjunction with other neurotrophic factors such as CNTF, BDNF, or NGF to prevent and/or reverse motor neuron degeneration in ALS patients.

The cdGF polypeptides of the present invention can also be used in the treatment of autonomic disorders of the peripheral nervous system, which include disorders affecting the innervation of smooth muscle and endocrine tissue (such as glandular tissue). For instance, cdGF compositions may be useful to treat tachycardia or atrial cardiac arrythmias which may arise from a degenerative condition of the nerves innervating the striated muscle of the heart.

Accordingly, compositions comprising cdGF homologs or other cdGF agents described herein may be employed to support, or alternatively, antagonize the survival and reprojection of several types of central and peripheral ganglionic neurons, sympathetic and sensory neurons, as well as motor neurons. To illustrate, such therapeutic compositions may be useful in treatments designed to rescue, for example, retinal ganglia, inner ear and accoustical nerves, and motorneurons, from lesion-induced death as well as guiding reprojection of these neurons after such damage. Such diseases and conditions include but are not limited to CNS trauma, infarction, infection (such as viral infection with varicella-zoster), metabolic disease, nutritional deficiency, toxic agents (such as cisplatin treatment). Moreover, certain of the cdGF agents (probably antagonistic forms) may be useful in the selective ablation of sensory neurons, for example, in the treatment of chronic pain syndromes.

cdGF can be used in nerve prostheses for the repair of central and peripheral nerve damage. In particular, where a crushed or severed axon is entubulated by use of a prosthetic device, cdGF polypeptides can be added to the prosthetic device to increase the rate of growth and regeneration of the dendritic processes. Exemplary nerve guidance channels are described in U.S. Pat. Nos. 5,092,871 and 4,955,892. Accordingly, a severed axonal process can be directed toward the nerve ending from which it was severed by a prosthesis nerve guide which contains, e.g. a semi-solid formulation containing a cdGF polypeptide or mimetic, or which is derivatized along the inner walls with a cdGF protein.

In yet another embodiment, the subject cdGF polypeptides can be used in the treatment of neoplastic or hyperplastic transformations, particularly of the central nervous system and lymphatic system. For instance, certain cdGF homologs are likely to be capable of inducing differentiation of transformed neuronal cells to become post-mitotic or possibly apoptotic. Treatment with other cdGF homologs may involve disruption of autocrine loops, such as TGF-$\beta$ or PDGF autostimulatory loops, believed to be involved in the neoplastic transformation of several neuronal tumors. cdGF homologs may, therefore, be of use in the treatment of, for example, malignant gliomas, medulloblastomas, neuroectodermal tumors, and ependymonas.

Yet another aspect of the present invention concerns the application of the discovery that cdGF proteins are likely induction signals involved in other vertebrate organogenic pathways in addition to neuronal differentiation as described above, having potential roles in other ectodermal patterning, as well as both mesodermal and endodermal differentiation processes. Thus, it is contemplated by the invention that compositions comprising cdGF proteins can also be utilized for both cell culture and therapeutic methods involving generation and maintenance of non-neuronal tissue, such as in controlling the development and maintenance of tissue from the digestive tract, liver, lungs, and other organs which derive from the primitive gut, as well as dorsal mesoderm-derived structures including muscular-skeletal tissues and connective tissue of the skin; intermediate mesoderm-derived structures, such as the kidney and other renal and urogenital tissues; and head mesenchymal and neural crest-derived tissue, such as cephalic connective tissue and skull and branchial cartilage, occular tissue, muscle and cardiac tissue. This should not be construed as a comprehensive list, and other tissues which may be affected by cdGF polypeptides are envisaged.

The cdGF polypeptides of the present invention, or pharmaceutically acceptable salts thereof, may be conveniently formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined emperically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the cdGF polypeptide, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations". Based on the above, such pharmaceutical formulations include, although not exclusively, solutions or freeze-dried powders of a cdGF polypeptide in association with one or more pharmaceutically acceptable vehicles or diluents, and contained in buffered media at a suitable pH and isosmotic with physiological fluids. For illustrative purposes only and without being limited by the same, possible compositions or formulations which may be prepared in the form of solutions for the treatment of nervous system disorders with a cdGF polypeptide are given in U.S. Pat. No. 5,218,094. In the case of freeze-dried preparations, supporting excipients such as, but not exclusively, mannitol or glycine may be used and appropriate buffered solutions of the desired volume will be provided so as to obtain adequate isotonic buffered solutions of the desired pH. Similar solutions may also be used for the pharmaceutical compositions of cdGF polypeptides in isotonic solutions of the desired volume and include, but not exclusively, the use of buffered saline solutions with phosphate or citrate at suitable concentrations so as to obtain at all times isotonic pharmaceutical preparations of the desired pH, (for example, neutral pH).

Methods of introduction of exogenous cdGF polypeptides at the site of treatment include, but are not limited to, intradermal, intramuscular, intraperitoneal, intravenous, subcutaneous, oral, and intranasal. In addition, it may be desirable to introduce the pharmaceutical compositions of the invention into the central nervous system by any suitable route, including intraventricular and intrathecal injection. Intraventricular injection may be facilitated by an intraventricular catheter, for example, attached to a reservoir, such as an Ommaya reservoir.

Methods of introduction may also be provided by rechargable or biodegradable devices, particularly where gradients of cdGF concentrations in a tissue is desired. Various slow release polymeric devices have been developed and tested in vivo in recent years for the controlled delivery of drugs, including proteinacious biopharmaceuticals. A variety of biocompatible polymers (including hydrogels), including both biodegradable and nondegradable polymers, can be used to form an implant for the sustained release of a cdGF at a particular target site. Such embodiments of the present invention can be used for the delivery of an exogenously purified cdGF polypeptides, which has been incorporated in the polymeric device, or for the delivery of cdGF polypeptides produced by a cell encapsulated in the polymeric device. The generation of such implants is generally known in the art. See, for example, *Concise Encylopedia of Medical & Dental Materials*, ed. by David Williams (MIT Press: Cambridge, Mass., 1990); the Sabel et al. U.S. Pat. No. 4,883,666; Aebischer et al. U.S. Pat. No. 4,892,538; Aebischer et al. U.S. Pat. No. 5,106,627; Lim U.S. Pat. No. 4,391,909; and Sefton U.S. Pat. No. 4,353,888.

In yet another embodiment of the present invention, the pharmaceutical cdGF polypeptide can be administered as part of a combinatorial therapy with other agents. For example, the combinatorial therapy can include a cdGF protein with at least one trophic factor. Exemplary trophic factors include nerve growth factor, cilliary neurotrophic growth factor, schwanoma-derived growth factor, glial growth factor, stiatal-derived neuronotrophic factor, platelet-derived growth factor, and scatter factor (HGF-SF).

Another aspect of the invention features transgenic non-human animals which express a heterologous cdGF gene of the present invention, or which have had one or more genomic cdGF gene(s) disrupted in at least one of the tissue or cell-types of the animal. Accordingly, the invention features an animal model for developmental diseases, which animal has a cdGF allele which is mis-expressed. For example, a mouse can be bred which has one or more cdGF alleles deleted or otherwise rendered inactive. Such a mouse model can then be used to study disorders arising from mis-expressed cdGF genes.

Another aspect of the present invention concerns transgenic animals which are comprised of cells (of that animal) which contain a transgene of the present invention and which preferably (though optionally) express an exogenous cdGF protein in one or more cells in the animal. The cdGF transgene can encode the wild-type form of the protein, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosiac expression of the subject polypeptide can be essential for many forms of lineage analysis and can additionally provide a means to assess the effects of, for example, lack of cdGF expression which might grossly alter development in small patches of tissue within an otherwise normal embryo. Toward this and, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of the subject cdGF polypeptide. For example, excision of a target sequence which interferes with the expression of a recombinent cdGF gene, such as one which encodes an antagonistic homolog, can be designed to activate expression of that gene. This interference with expression of the protein can result from a variety of mechanisms, such as spatial separation of the cdGF gene from the promoter element or an internal stop codon. Moreover, the transgene can be made wherein the coding sequence of the gene is flanked recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

In an illustrative embodiment, either the cre/loxP recombinase system of bacteriophage P1 (Lakso et al. (1992) *PNAS* 89: 6232–6236; Orban et al. (1992) *PNAS* 89: 6861–6865) or the FLP recombinase system of *Saccharomyces cerevisiae* (O'Gorman et al. (1991) *Science* 251: 1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) *J. Biol. Chem.* 259: 1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of the recombinant cdGF protein can be regulated via control of recombinase expression.

Use of the cre/loxP recombinase system to regulate expression of a recombinant cdGF protein requires the construction of a transgenic animal containing transgenes encoding both the Cre recombinase and the subject protein. Animals containing both the Cre recombinase and a recombinant cdGF gene can be provided through the construction of "double" transgenic animals. A convenient method for providing such animals is to mate two transgenic animals each containing a transgene, e.g., a cdGF gene and recombinase gene.

One advantage derived from initially constructing transgenic animals containing a cdGF transgene in a recombinase-mediated expressible format, particularly derives from the likelihood that the subject protein will be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues. Thus, the creation of a founder population in which, for example, an antagonistic cdGF transgene is silent will allow the study of progeny from that founder in which disruption of cdGF mediated induction in a particular tissue or at developmental stages would result in, for example, a lethal phenotype.

Similar conditional transgenes can be provided using prokaryotic promoter sequences which require prokaryotic proteins to be simultaneous expressed in order to facilitate expression of the transgene. Exemplary promoters and the corresponding trans-activating prokaryotic proteins are given in U.S. Pat. No. 4,833,080. Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, the cdGF transgene could remain silent into adulthood until "turned on" by the introduction of the trans-activator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The zygote is the best target for micro-injection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al. (1985) *PNAS* 82: 4438–4442). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) *PNAS* 73: 1260–1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82: 6927–6931; Van der Putten et al. (1985) *PNAS* 82: 6148–6152). Transfection is easily and efficiently obtained by culturing the blastomeres on a monolayer of virus-producing cells (Van der Putten, supra; Stewart et al. (1987) *EMBO J.* 6: 383–388). Alternatively, infection can be performed at a later stage. Virus or virus-producing cells can be injected into the blastocoele (Jahner et al. (1982) *Nature* 298: 623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292: 154–156; Bradley et al. (1984) *Nature* 309: 255–258; Gossler et al. (1986) *PNAS* 83: 9065–9069; and Robertson et al. (1986) *Nature* 322: 445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240: 1468–1474.

Methods of making knock-out or disruption transgenic animals are also generally known. See, for example, *Manipulating the Mouse Embryo*, (Cold Spring Harbor Laboratory Press, Cold Spring Harbor, N.Y., 1986). Recombinase dependent knockouts can also be generated, e.g. by homologous recombination to insert recombinase target sequences flanking portions of an endogenous cdGF gene, such that tissue specific and/or temporal control of inactivation of a cdGF allele can be controlled as above.

The invention now being generally described, it will be more readily understood by reference to the following examples which are included merely for purposes of illustration of certain aspects and embodiments of the present invention, and are not intended to limit the invention.

Cloning and Sequencing of cdGF

A PCR based strategy was used to clone each of the cdGF-1 and cdGF-2. Primers were designed according to two conserved regions in Heregulins/GGF/ARIA amino acid sequences: one in the Ig-like domain and the other in the EGF-like domain. An adult rat cerebellum cDNA library were amplified by PCR using the above two primers. PCR products were sequenced and inspected for sequence homology with Heregulins. One positive clone was identified.

This PCR fragment was used as a probe to screen the same cerebellum cDNA library, and several positive clones were identified. In particular, two partial, overlapping clones, designated clone 2b and 2d, were identified as encoding the cdGF-1 protein. Clone 2b corresponds to the nucleic acid sequence 1–1252 of SEQ ID No. 1. Clone 2d corresponds to nucleotides 592–3441 of SEQ ID No. 1.

Another clone, designated clone 3, was a partial clone corresponding to the C-terminal fragment of the cdGF protein, which fragment lacked the Spacer 1 sequence and the N-terminal half of the Ig-like domain. Moreover, the nucleic acid sequence revealed a 77 nucleotide insert (see FIG. 2) at the 3' end of the EGF-like coding sequence which results in a frame shift and, consequently, a stop codon to form a truncated protein lacking transmembrane and cytoplasmic domains.

Each of the clones 2b, 2d and 3 were present as inserts in the pBluescript II phagemid vector (Stratagene, La Jolla, Calif.) as EcorRI inserts. Both the cdGF-1 and cdGF-2 proteins shares only about 50 percent homology with any of the ARIA, heregulin, NDF or GGF proteins. A deposit of a nucleic acid library containing the pBluescript clones 2b, 2d and 3 was made with the American Type Culture Collection (Rockville, Md.) on Sep., 8 1995, under the terms of the Budapest Treaty. ATCC Accession number 97274 has been assigned to the deposit. Each of the clones can be separately isolated from the ATCC deposit by, for example, PCR amplification using primers sets in which at least one primer anneals to a nucleic acid sequence unique to only one clone of the library. To illustrate, the primer set 5'-ATGCTCGCCTGCTACTCGCCC (SEQ ID No: 9) and 5'-GCCGGACACATGTTCTGCC (SEQ ID No: 10) can be used to amplify the coding sequence of clone 2b from the library. Likewise, the primer sets 5'-CACTGACTGCGCAACCCGG (SEQ ID No: 11) and 5'-GGCCTTAGAGGGGCCCGGA (SEQ ID No: 12), and 5'-AAAGAACTCACGGCTACAGTTC (SEQ ID No: 13) and 5'-CCTTTAATTCAAATCCAAGGT (SEQ ID No: 14) can be used to amplify the coding sequences in clone 2d and clone 3, respectively.

Moreover, it will be apparent that a full length construct can be generated for each of the cdGF-1 and cdGF-2 homologs by annealing a fragment from clone 2b with a fragment generated from clone 2d or clone 3, respectively. For example, the primers 5'-GAATTCGGCACGAGGGCAG (SEQ ID No: 15) and 5'-CTCATTGCACTTCCGGGCG (SEQ ID No: 16) can be used to provide a double stranded fragment of clone 2b corresponding to Met1-Glu255, which is common to both cdGF-1 and cdGF-2. As above, the primer sets 5'-CACTGACTGCGCAAC-CCGG (SEQ ID No: 11) and 5'-GGCCTTAGAGGGGCCCGGA (SEQ ID No: 12), and 5'-AAAGAACTCACGGCTACAGTTC (SEQ ID No: 13) and 5'-CCTTTAATTCAAATCCAAGGT (SEQ ID No: 14) can be used to double stranded fragments of clone 2d and clone 3, respectively. The clone 2b PCR products are mixed with those of either clone 2d or clone 3 under denaturing conditions, and then renatured. Upon renaturation, the single-stranded regions are filled in by incubating with a DNA polymerase, dNTPs, and DNA ligase; and the resulting cdGF-encoding gene subsequently cloned into an expression vector to provide the proteins represented by either SEQ ID No. 2 or 4.

Expression of CDGF mRNA in Adult Rat Tissues

The prior art technique of RT-PCR is a very sensitive method to detect the presence of mRNAs in a tissue, though it does not give quantitative information. Two primers flanking the EGF-like domain of each cdGF were used. Messenger RNAs from various adult rat tissues were prepared, and RT-PCR were performed with these unique probes. Preliminary results indicate that cdGF-1 is present in almost every tissues examined so far, while cdGF-2 is only detected in the central nervous system.

Northern Blot analysis is less sensitive, but gives information about relative expression level. Again mRNA from adult rat tissues were used in the experiments. A probe corresponding to the EGF-like domain was used. This probe can specifically detect both cdGF-1 and cdGF-2 mRNA, but can not distinguish between them. Preliminary results indicate that cdGFs are expressed in adult rat central nervous system, with the highest expression in the cerebellum. No signal was detected in non-neuronal tissues in this experiment, indicating that cdGF expression in these tissues is low compared to the central nervous system.

Interaction of CDGF-1 with erbB Receptors

The insert of clone 2b, which contains from the putative signal peptide to the beginning of the intracellular domain, was subcloned into an expression vector. COS-7 cells were transfected with the expression vector, and conditioned medium was collected.

MDA-MB-453 cells, which contain both erbB2 and erbB4 receptors were obtained from a commercial source. Conditioned mediums were applied to MDA-MB-453 cells, and total cell lysates were subjected to Western Blot analysis with antibodies against phospho-tyrosine. A 185 kd protein band, which corresponding to the molecular weights of both erbB2 and erbB4, was phosphorylated by the addition of conditioned medium. These results suggest that recombinant cdGF-1 proteins is biologically active and interact with erbB2 and/or erbB4.

Various fragments of cdGFs have been subcloned into an *E. coli* expression vector and recombinant proteins were produced. These fragments correspond to: (i) the Ig-like domain and the EGF-like domain of cdGF-1; (ii) the EGF-like domain of cdGF-1; (iii) the EGF-like domain of cdGF-2.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

I claim:

1. An isolated or recombinant cdGF polypeptide comprising a cdGF amino acid sequence corresponding to amino acid residues 1–314 of SEQ ID No. 2.

2. An isolated or recombinant cdGF polypeptide, which polypeptide can be encoded by a nucleic acid molecule which hybridizes under highly stringent conditions to a second nucleic acid molecule, said second nucleic acid molecule comprising the noncoding strand of SEQ ID NO: 1 and said highly stringent conditions comprising hybridization in 6.0×sodium chloride/sodium citrate (SSC), followed by washing in 0.2×SSC at 50° C., and which polypeptide binds to an erbB2, erbB3 or erbB4 receptor.

3. An isolated or recombinant cdGF polypeptide comprising the amino acid sequence of SEQ ID No: 2.

4. An isolated or recombinant cdGF polypeptide, which polypeptide can be encoded by a nucleic acid molecule which hybridizes under highly stringent conditions to a second nucleic acid molecule, said second nucleic acid molecule comprising the noncoding strand of SEQ ID No. 5, and said highly stringent conditions comprising hybridization in 6.0×SSC, followed by washing in 0.2×SSC at 50° C., and which polypeptide binds to an erbB2, erbB3 or erbB4 receptor.

5. An isolated or recombinant cdGF polypeptide comprising the amino acid sequence of SEQ ID NO: 4.

6. An isolated or recombinant cdGF polypeptide comprising a CDGF amino acid sequence corresponding to amino acid residues 1–314 of SEQ ID NO: 2, but which lacks from 5 to 15 amino acid residues from The N-terminus of polypeptide of SEQ ID NO: 2.

7. The isolated or recombinant cdGF polypeptide of claim 6, which polypeptide is glycosylated.

8. The isolated or recombinant cdGF polypeptide of claim 6, which polypeptide is a fusion protein further comprising, in addition to said cdGF amino acid sequence, a second polypeptide sequence having an amino acid sequence unrelated to said cdGF amino acid sequence.

9. The isolated or recombinant polypeptide of claim 8, wherein said fusion protein includes, as a second polypeptide sequence, a polypeptide which functions as a detectable label for detecting the presence of said fusion protein or as a matrix-binding domain for immobilizing said fusion protein.

10. An isolated or recombinant cdGF polypeptide comprising the amino acid sequence of SEQ ID No: 2, but which lacks from 5 to 15 amino acid residues from The N-terminus of the polypeptide of SEQ ID NO: 2.

11. An isolated or recombinant cdGF polypeptide comprising the amino acid sequence of SEQ ID No: 4, but which lacks from 5 to 15 amino acid residues from the N-terminus of the polypeptide of SEQ ID NO: 4.

* * * * *

```
                          SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
          (A) LENGTH: 3441 base pairs
          (B) TYPE: nucleic acid
          (C) STRANDEDNESS: double
          (D) TOPOLOGY: linear (ii) MOLECULE TYPE: cDNA (ix) FEATURE:
          (A) NAME/KEY: CDS
          (B) LOCATION: 180..2441

(xi) SEQUENCE DESCRIPTION: SEQ ID NO:1:

GAATTCGGCA CGAGGGCAGC ACCACCACCA CCAGCAGCAG CGAGAACAGC GGCAGCAACA        60

GCGGCAGCAT CTTCCGTCCC GCTGCGCCCC CAGAGCCGCG GCCGCAGCCA CAGCCGCAGC       120

CCCGCAGCCC CGCAGCCCGG AGAGCCGCCG CCCGCTCGCG AGCCGCAGCC GCCGGCGGC        179

ATG AGG CGC GAC CCG GCC CCC GGC TTC TCG ATG CTG CTC TTC GGT GTG        227
Met Arg Arg Asp Pro Ala Pro Gly Phe Ser Met Leu Leu Phe Gly Val
  1               5                  10                  15

TCA CTC GCC TGC TAC TCG CCC AGC CTC AAG TCC GTG CAG GAC CAG GCG        275
Ser Leu Ala Cys Tyr Ser Pro Ser Leu Lys Ser Val Gln Asp Gln Ala
             20                  25                  30

TAC AAG GCA CCC GTG GTG GTG GAG GGC AAG GTA CAG GGA CTG GCC CCG        323
Tyr Lys Ala Pro Val Val Val Glu Gly Lys Val Gln Gly Leu Ala Pro
         35                  40                  45

GCA GGC GGT TCC AGC TCT AAC AGC ACC CGA GAG CCT CCC GCC TCG GGT        371
Ala Gly Gly Ser Ser Ser Asn Ser Thr Arg Glu Pro Pro Ala Ser Gly
     50                  55                  60

CGG GTG GCG CTG GTG AAG GTG CTG GAC AAG TGG CCG CTC CGG AGC GGG        419
Arg Val Ala Leu Val Lys Val Leu Asp Lys Trp Pro Leu Arg Ser Gly
 65                  70                  75                  80

GGG CTG CAG CGC GAG CAG GTG ATC AGC GTG GGC TCC TGC GCG CCG CTC        467
Gly Leu Gln Arg Glu Gln Val Ile Ser Val Gly Ser Cys Ala Pro Leu
                 85                  90                  95

GAA AGG AAC CAG CGC TAC ATC TTT TTC CTG GAG CCC ACC GAG CAG CCC        515
Glu Arg Asn Gln Arg Tyr Ile Phe Phe Leu Glu Pro Thr Glu Gln Pro
            100                 105                 110

TTA GTT TTT AAG ACA GCC TTT GCC CCG GTC GAC CCT AAC GGC AAA AAC        563
Leu Val Phe Lys Thr Ala Phe Ala Pro Val Asp Pro Asn Gly Lys Asn
        115                 120                 125

ATC AAG AAA GAG GTG GGC AAG ATC CTG TGC ACT GAC TGC GCA ACC CGG        611
Ile Lys Lys Glu Val Gly Lys Ile Leu Cys Thr Asp Cys Ala Thr Arg
    130                 135                 140

CCC AAG CTG AAG AAG ATG AAG AGT CAG ACA GGA GAG GTG GGC GAG AAG        659
Pro Lys Leu Lys Lys Met Lys Ser Gln Thr Gly Glu Val Gly Glu Lys
145                 150                 155                 160

CAG TCG CTC AAG TGT GAG GCG GCG GCG GGG AAC CCC CAG CCC TCC TAT        707
Gln Ser Leu Lys Cys Glu Ala Ala Ala Gly Asn Pro Gln Pro Ser Tyr
```

```
                            165                 170                 175
CGA TGG TTC AAG GAC GGC AAG GAG CTC AAC CGG AGT CGT GAC ATT CGC         755
Arg Trp Phe Lys Asp Gly Lys Glu Leu Asn Arg Ser Arg Asp Ile Arg
        180                 185                 190

ATC AAG TAT GGC AAC GGC AGA AAG AAC TCA CGG CTA CAG TTC AAC AAA         803
Ile Lys Tyr Gly Asn Gly Arg Lys Asn Ser Arg Leu Gln Phe Asn Lys
        195                 200                 205

GTG AAG GTG GAG GAC GCT GGA GAG TAC GTC TGT GAG GCT GAG AAC ATC         851
Val Lys Val Glu Asp Ala Gly Glu Tyr Val Cys Glu Ala Glu Asn Ile
        210                 215                 220

CTT GGG AAG GAC ACT GTG AGG GGC CGG CTC CAT GTC AAC AGT GTG AGC         899
Leu Gly Lys Asp Thr Val Arg Gly Arg Leu His Val Asn Ser Val Ser
225                 230                 235                 240

ACC ACT CTG TCG TCC TGG TCG GGG CAC GCC CGG AAG TGC AAT GAG ACA         947
Thr Thr Leu Ser Ser Trp Ser Gly His Ala Arg Lys Cys Asn Glu Thr
                245                 250                 255

GCC AAG TCC TAC TGT GTG AAT GGA GGC GTG TGC TAC TAC ATC GAA GGC         995
Ala Lys Ser Tyr Cys Val Asn Gly Gly Val Cys Tyr Tyr Ile Glu Gly
            260                 265                 270

ATC AAC CAA CTC TCC TGC AAG TGT CCT GTG GGA TAC ACC GGG GAC AGG        1043
Ile Asn Gln Leu Ser Cys Lys Cys Pro Val Gly Tyr Thr Gly Asp Arg
        275                 280                 285

TGT CAG CAG TTC GCA ATG GTC AAC TTC TCC AAG CAC CTT GGA TTT GAA        1091
Cys Gln Gln Phe Ala Met Val Asn Phe Ser Lys His Leu Gly Phe Glu
        290                 295                 300

TTA AAG GAG GCT GAG GAG CTG TAC CAG AAG AGA GTC CTG ACA ATT ACC        1139
Leu Lys Glu Ala Glu Glu Leu Tyr Gln Lys Arg Val Leu Thr Ile Thr
305                 310                 315                 320

GGC ATC TGT GTG GCT CTG CTG GTC GTG GGC ATC GTC TGT GTG GTC GCC        1187
Gly Ile Cys Val Ala Leu Leu Val Val Gly Ile Val Cys Val Val Ala
                325                 330                 335

TAC TGC AAG ACT AAA AAA CAG AGG AGG CAA ATG CAT CAC CAT CTC CGG        1235
Tyr Cys Lys Thr Lys Lys Gln Arg Arg Gln Met His His His Leu Arg
            340                 345                 350

CAG AAC ATG TGT CCG GCC CAC CAG AAC CGA AGC CTG GCC AAT GGG CCC        1283
Gln Asn Met Cys Pro Ala His Gln Asn Arg Ser Leu Ala Asn Gly Pro
        355                 360                 365

AGC CAC CCT CGG CTG GAC CCT GAG GAG ATC CAG ATG GCA GAT TAC ATT        1331
Ser His Pro Arg Leu Asp Pro Glu Glu Ile Gln Met Ala Asp Tyr Ile
        370                 375                 380

TCC AAA AAT GTG CCA GCT ACA GAC CAT GTG ATC CGG AGG GAA GCT GAG        1379
Ser Lys Asn Val Pro Ala Thr Asp His Val Ile Arg Arg Glu Ala Glu
385                 390                 395                 400

ACC ACA TTT TCT GGG AGC CAC TCC TGT TCA CCC TCT CAC CAC TGT TCC        1427
Thr Thr Phe Ser Gly Ser His Ser Cys Ser Pro Ser His His Cys Ser
                405                 410                 415

ACA GCC ACA CCC ACC TCC AGC CAC AGA CAT GAG AGC CAC ACG TGG AGC        1475
Thr Ala Thr Pro Thr Ser Ser His Arg His Glu Ser His Thr Trp Ser
            420                 425                 430

TTG GAA CGT TCG GAG AGC CTG ACC TCG GAT TCC CAG TCA GGC ATC ATG        1523
Leu Glu Arg Ser Glu Ser Leu Thr Ser Asp Ser Gln Ser Gly Ile Met
        435                 440                 445

CTA TCA TCA GTG GGC ACC AGC AAG TGC AAC AGC CCA GCA TGT GTG GAG        1571
Leu Ser Ser Val Gly Thr Ser Lys Cys Asn Ser Pro Ala Cys Val Glu
450                 455                 460

GCA CGG GCA CGG AGG GCA GCA GCC TAC AGC CAG GAG GAG CGA GCC AGG        1619
Ala Arg Ala Arg Arg Ala Ala Ala Tyr Ser Gln Glu Glu Arg Ala Arg
465                 470                 475                 480

GCT GCC ATG CCA CCC TAC CAC GAC TCC ATA GAC TCG CTG CGT GAC TCC        1667
Ala Ala Met Pro Pro Tyr His Asp Ser Ile Asp Ser Leu Arg Asp Ser
```

-continued

```
                485                 490                 495
CCA CAC AGT GAG AGG TAC GTG TCA GCC CTG ACC ACG CCC GCG CGC CTT       1715
Pro His Ser Glu Arg Tyr Val Ser Ala Leu Thr Thr Pro Ala Arg Leu
            500                 505                 510

TCG CCC GTG GAC TTC CAC TAC TCG CTG GCC ACC CAG GTG CCG ACT TTC       1763
Ser Pro Val Asp Phe His Tyr Ser Leu Ala Thr Gln Val Pro Thr Phe
            515                 520                 525

GAG ATC ACG TCG CCC AAC TCT GCC CAC GCC GTG TCG CTG CCA CCC GCA       1811
Glu Ile Thr Ser Pro Asn Ser Ala His Ala Val Ser Leu Pro Pro Ala
            530                 535                 540

GCG CCC ATC AGC TAC CGC CTA GCG GAG CAG CAG CCG CTC CTG GGG CAC       1859
Ala Pro Ile Ser Tyr Arg Leu Ala Glu Gln Gln Pro Leu Leu Gly His
545                 550                 555                 560

CCA GCG CCG CCC GGC CCG GGG CCA GGG CCC GGA GCG GAC ATG CAG CGC       1907
Pro Ala Pro Pro Gly Pro Gly Pro Gly Pro Gly Ala Asp Met Gln Arg
                565                 570                 575

AGC TAC GAC AGC TAC TAC TAC CCG GCG GCG GGG CCC GGG CCG CGG CGG       1955
Ser Tyr Asp Ser Tyr Tyr Tyr Pro Ala Ala Gly Pro Gly Pro Arg Arg
            580                 585                 590

GGC GCC TGC GCG CTG GGC GGC AGT TTG GGC AGC CTG CCC GCC AGC CCC       2003
Gly Ala Cys Ala Leu Gly Gly Ser Leu Gly Ser Leu Pro Ala Ser Pro
595                 600                 605

TTC CAC ATC CCG GAG GAC GAC GAG TAC GAG ACC ACG CAG GAG TGC GCG       2051
Phe His Ile Pro Glu Asp Asp Glu Tyr Glu Thr Thr Gln Glu Cys Ala
610                 615                 620

CCC CCG CCA CCG CCG CGG CCG CGC ACG CGC GGC GCG TCC CGC AGG ACG       2099
Pro Pro Pro Pro Pro Arg Pro Arg Thr Arg Gly Ala Ser Arg Arg Thr
625                 630                 635                 640

TCG GCG GGG CCG CGG CGC TGG CGG CGC TCC CGC CTC AAC GGG TTG GCT       2147
Ser Ala Gly Pro Arg Arg Trp Arg Arg Ser Arg Leu Asn Gly Leu Ala
                645                 650                 655

GCG CAG CGC GCA CGC GCA GCG CGG GAC TCG CTG TCG TTG AGC AGC GGT       2195
Ala Gln Arg Ala Arg Ala Ala Arg Asp Ser Leu Ser Leu Ser Ser Gly
            660                 665                 670

TCG GGC TGC GGC TCG GCG TCG GCC TCG GAC GAC GAT GCG GAC GAC GCG       2243
Ser Gly Cys Gly Ser Ala Ser Ala Ser Asp Asp Asp Ala Asp Asp Ala
            675                 680                 685

GAC GGG GCG CTG GCG GCC GAG AGC ACG CCT TTC CTC GGC CTG CGA GCG       2291
Asp Gly Ala Leu Ala Ala Glu Ser Thr Pro Phe Leu Gly Leu Arg Ala
690                 695                 700

GCG CAC GAC GCG CTG CGC TCG GAC TCG CCG CCG CTC TGC CCG GCG GCG       2339
Ala His Asp Ala Leu Arg Ser Asp Ser Pro Pro Leu Cys Pro Ala Ala
705                 710                 715                 720

GAC AGC AGG ACT TAC TAC TCC CTG GAC AGC CAC AGC ACG CGC GCC AGC       2387
Asp Ser Arg Thr Tyr Tyr Ser Leu Asp Ser His Ser Thr Arg Ala Ser
                725                 730                 735

AGC AGA CAC AGC CGG GGG CCG CCC ACG AGG GCA AAG CAG GAC TCC GGG       2435
Ser Arg His Ser Arg Gly Pro Pro Thr Arg Ala Lys Gln Asp Ser Gly
            740                 745                 750

CCC CTC TAAGGCCTCC CGCCTCGCCC GCCTCACGTC TCCGAGGAGA GCGGAGACCA       2491
Pro Leu
CCGACTGGAG AGGGAAAAAG GAGCGAACAA AGAAATAAAA ATATTTTTAT TTTCTATAAA    2551

AGGAAAAAAG TATAACAAAA TGTTTTATTT TCATTTTAGC AAAAAAAATT GTCTTATAAT    2611

ACTAGCTAAC GGCAAAGACG TTTTTATAGG GAAACTATTT ATATGTAACA TCCTGATTTA    2671

CAGCTTCGGA AAAAAAAAAG AAACAACAAA AAAAAAAAAG AGAGATGGGC CAATTTTTTT    2731

GACTCTTTAA TAGAAACCTA TATTGTGGTG CCTTTTGCTG TACGCTAATC TGGGGCTCCT    2791

GGAGAGCCGT CTGGGGTGCA GTGTGGGGAT GGGCGCTTAT AGGATCCCAA ACTGGTGGGG    2851
```

```
GTGAGAAAAG GCAGGTAAAG AAGAGACTGT GAGGTTCGAA TGGTTCTGAG GGTAATGAAC    2911

AATGAGGAAG AAGATGAAGA TAAGACGAAA TTTTATCTTC CCCAGTCCAG ATCTGGAGTC    2971

CTGAACAGAG AGGGCAGGGA TCCTAGCCTT CGAGCTGGAA TTGAGATGGG GTTATTTCCA    3031

GGAGGAGACA CAGGCCTCCC GTTACAGCAA CTAGAATGGG GAAGGTCCTC CCCAGCCCTC    3091

ACAGCTGCTA AGGGAAAGAG GACAGAGAAG GCTGTCTCCC CACCAGCCCC CCCGCCTAGG    3151

GAGGGGGCAG CTCTACCAGG GGCCCAACCT TCATGGCTCC TCCTCCCTGC GGCCTCCAGG    3211

ATGTCCTCTG TCCTCTGCAG CACCTTCGTT TACAGGTCGT CTTTTCTATT TTACGCCTGC    3271

ATGTCCTTCG CATTTCAGAT TCTTTAGATT GAATGCATGG TCACGCTGGG ACCCGGAAGA    3331

GCCACTCCAA CAGTGTATTC GATTCCCCTT TTAGCAATAA AGTAACACCA TATCCTCACA    3391

GCCCAGCTCC CAACCCACCT ATGACTTTCA TCTTCCCTCT TGCCGAATTC               3441
```

(2) INFORMATION FOR SEQ ID NO:2:

(i) SEQUENCE CHARACTERISTICS:
        (A) LENGTH: 754 amino acids
        (B) TYPE: amino acid
        (D) TOPOLOGY: linear (ii) MOLECULE TYPE: protein (xi) SEQUENCE DESCRIPTION: SEQ ID NO:2:

```
Met Arg Arg Asp Pro Ala Pro Gly Phe Ser Met Leu Leu Phe Gly Val
 1               5                  10                  15

Ser Leu Ala Cys Tyr Ser Pro Ser Leu Lys Ser Val Gln Asp Gln Ala
            20                  25                  30

Tyr Lys Ala Pro Val Val Val Glu Gly Lys Val Gln Gly Leu Ala Pro
        35                  40                  45

Ala Gly Gly Ser Ser Ser Asn Ser Thr Arg Glu Pro Pro Ala Ser Gly
    50                  55                  60

Arg Val Ala Leu Val Lys Val Leu Asp Lys Trp Pro Leu Arg Ser Gly
65                  70                  75                  80

Gly Leu Gln Arg Glu Gln Val Ile Ser Val Gly Ser Cys Ala Pro Leu
                85                  90                  95

Glu Arg Asn Gln Arg Tyr Ile Phe Phe Leu Glu Pro Thr Glu Gln Pro
            100                 105                 110

Leu Val Phe Lys Thr Ala Phe Ala Pro Val Asp Pro Asn Gly Lys Asn
        115                 120                 125

Ile Lys Lys Glu Val Gly Lys Ile Leu Cys Thr Asp Cys Ala Thr Arg
    130                 135                 140

Pro Lys Leu Lys Lys Met Lys Ser Gln Thr Gly Glu Val Gly Glu Lys
145                 150                 155                 160

Gln Ser Leu Lys Cys Glu Ala Ala Gly Asn Pro Gln Pro Ser Tyr
                165                 170                 175

Arg Trp Phe Lys Asp Gly Lys Glu Leu Asn Arg Ser Arg Asp Ile Arg
            180                 185                 190

Ile Lys Tyr Gly Asn Gly Arg Lys Asn Ser Arg Leu Gln Phe Asn Lys
        195                 200                 205

Val Lys Val Glu Asp Ala Gly Glu Tyr Val Cys Glu Ala Glu Asn Ile
    210                 215                 220

Leu Gly Lys Asp Thr Val Arg Gly Arg Leu His Val Asn Ser Val Ser
225                 230                 235                 240

Thr Thr Leu Ser Ser Trp Ser Gly His Ala Arg Lys Cys Asn Glu Thr
                245                 250                 255
```

-continued

```
Ala Lys Ser Tyr Cys Val Asn Gly Gly Val Cys Tyr Tyr Ile Glu Gly
            260                 265                 270

Ile Asn Gln Leu Ser Cys Lys Cys Pro Val Gly Tyr Thr Gly Asp Arg
            275                 280                 285

Cys Gln Gln Phe Ala Met Val Asn Phe Ser Lys His Leu Gly Phe Glu
290                 295                 300

Leu Lys Glu Ala Glu Glu Leu Tyr Gln Lys Arg Val Leu Thr Ile Thr
305                 310                 315                 320

Gly Ile Cys Val Ala Leu Leu Val Val Gly Ile Val Cys Val Val Ala
                325                 330                 335

Tyr Cys Lys Thr Lys Lys Gln Arg Arg Gln Met His His His Leu Arg
                340                 345                 350

Gln Asn Met Cys Pro Ala His Gln Asn Arg Ser Leu Ala Asn Gly Pro
            355                 360                 365

Ser His Pro Arg Leu Asp Pro Glu Glu Ile Gln Met Ala Asp Tyr Ile
370                 375                 380

Ser Lys Asn Val Pro Ala Thr Asp His Val Ile Arg Arg Glu Ala Glu
385                 390                 395                 400

Thr Thr Phe Ser Gly Ser His Ser Cys Ser Pro Ser His Cys Ser
                405                 410                 415

Thr Ala Thr Pro Thr Ser Ser His Arg His Glu Ser His Thr Trp Ser
            420                 425                 430

Leu Glu Arg Ser Glu Ser Leu Thr Ser Asp Ser Gln Ser Gly Ile Met
            435                 440                 445

Leu Ser Ser Val Gly Thr Ser Lys Cys Asn Ser Pro Ala Cys Val Glu
450                 455                 460

Ala Arg Ala Arg Arg Ala Ala Tyr Ser Gln Glu Glu Arg Arg Arg
465                 470                 475                 480

Ala Ala Met Pro Pro Tyr His Asp Ser Ile Asp Ser Leu Arg Asp Ser
                485                 490                 495

Pro His Ser Glu Arg Tyr Val Ser Ala Leu Thr Thr Pro Ala Arg Leu
            500                 505                 510

Ser Pro Val Asp Phe His Tyr Ser Leu Ala Thr Gln Val Pro Thr Phe
            515                 520                 525

Glu Ile Thr Ser Pro Asn Ser Ala His Ala Val Ser Leu Pro Pro Ala
530                 535                 540

Ala Pro Ile Ser Tyr Arg Leu Ala Glu Gln Gln Pro Leu Leu Gly His
545                 550                 555                 560

Pro Ala Pro Pro Gly Pro Gly Pro Gly Ala Asp Met Gln Arg
                565                 570                 575

Ser Tyr Asp Ser Tyr Tyr Pro Ala Ala Gly Pro Gly Pro Arg Arg
            580                 585                 590

Gly Ala Cys Ala Leu Gly Gly Ser Leu Gly Ser Leu Pro Ala Ser Pro
            595                 600                 605

Phe His Ile Pro Glu Asp Asp Glu Tyr Glu Thr Thr Gln Glu Cys Ala
610                 615                 620

Pro Pro Pro Pro Pro Arg Pro Arg Thr Arg Gly Ala Ser Arg Arg Thr
625                 630                 635                 640

Ser Ala Gly Pro Arg Arg Trp Arg Arg Ser Arg Leu Asn Gly Leu Ala
                645                 650                 655

Ala Gln Arg Ala Arg Ala Arg Asp Ser Leu Ser Leu Ser Ser Gly
            660                 665                 670

Ser Gly Cys Gly Ser Ala Ser Ala Ser Asp Asp Asp Ala Asp Ala
            675                 680                 685
```

```
Asp Gly Ala Leu Ala Ala Glu Ser Thr Pro Phe Leu Gly Leu Arg Ala
    690                 695                 700

Ala His Asp Ala Leu Arg Ser Asp Ser Pro Leu Cys Pro Ala Ala
705                 710                 715                 720

Asp Ser Arg Thr Tyr Tyr Ser Leu Asp Ser His Ser Thr Arg Ala Ser
                725                 730                 735

Ser Arg His Ser Arg Gly Pro Pro Thr Arg Ala Lys Gln Asp Ser Gly
            740                 745                 750

Pro Leu (2) INFORMATION FOR SEQ ID NO:3:

(i) SEQUENCE CHARACTERISTICS:
        (A) LENGTH: 993 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..990

(xi) SEQUENCE DESCRIPTION: SEQ ID NO:3:

ATG AGG CGC GAC CCG GCC CCC GGC TTC TCG ATG CTC CTC TTC GGT GTG        48
Met Arg Arg Asp Pro Ala Pro Gly Phe Ser Met Leu Leu Phe Gly Val
1               5                   10                  15

TCA CTC GCC TGC TAC TCG CCC AGC CTC AAG TCC GTG CAG GAC CAG GCG        96
Ser Leu Ala Cys Tyr Ser Pro Ser Leu Lys Ser Val Gln Asp Gln Ala
                20                  25                  30

TAC AAG GCA CCC GTG GTG GTG GAG GGC AAG GTA CAG GGA CTG GCC CCG       144
Tyr Lys Ala Pro Val Val Val Glu Gly Lys Val Gln Gly Leu Ala Pro
            35                  40                  45

GCA GGC GGT TCC AGC TCT AAC AGC ACC CGA GAG CCT CCC GCC TCG GGT       192
Ala Gly Gly Ser Ser Ser Asn Ser Thr Arg Glu Pro Pro Ala Ser Gly
    50                  55                  60

CGG GTG GCG CTG GTG AAG GTG CTG GAC AAG TGG CCG CTC CGG AGC GGG       240
Arg Val Ala Leu Val Lys Val Leu Asp Lys Trp Pro Leu Arg Ser Gly
65                  70                  75                  80

GGG CTG CAG CGC GAG CAG GTG ATC AGC GTG GGC TCC TGC GCG CCG CTC       288
Gly Leu Gln Arg Glu Gln Val Ile Ser Val Gly Ser Cys Ala Pro Leu
                85                  90                  95

GAA AGG AAC CAG CGC TAC ATC TTT TTC CTG GAG CCC ACC GAG CAG CCC       336
Glu Arg Asn Gln Arg Tyr Ile Phe Phe Leu Glu Pro Thr Glu Gln Pro
            100                 105                 110

TTA GTT TTT AAG ACA GCC TTT GCC CCG GTC GAC CCT AAC GGC AAA AAC       384
Leu Val Phe Lys Thr Ala Phe Ala Pro Val Asp Pro Asn Gly Lys Asn
        115                 120                 125

ATC AAG AAA GAG GTG GGC AAG ATC CTG TGC ACT GAC TGC GCA ACC CGG       432
Ile Lys Lys Glu Val Gly Lys Ile Leu Cys Thr Asp Cys Ala Thr Arg
130                 135                 140

CCC AAG CTG AAG AAG ATG AAG AGT CAG ACA GGA GAG GTG GGC GAG AAG       480
Pro Lys Leu Lys Lys Met Lys Ser Gln Thr Gly Glu Val Gly Glu Lys
145                 150                 155                 160

CAG TCG CTC AAG TGT GAG GCG GCG GCG GGG AAC CCC CAG CCC TCC TAT       528
Gln Ser Leu Lys Cys Glu Ala Ala Ala Gly Asn Pro Gln Pro Ser Tyr
                165                 170                 175

CGA TGG TTC AAG GAC GGC AAG GAG CTC AAC CGG AGT CGT GAC ATT CGC       576
Arg Trp Phe Lys Asp Gly Lys Glu Leu Asn Arg Ser Arg Asp Ile Arg
            180                 185                 190
```

```
ATC AAG TAT GGC AAC GGC AGA AAG AAC TCA CGG CTA CAG TTC AAC AAA    624
Ile Lys Tyr Gly Asn Gly Arg Lys Asn Ser Arg Leu Gln Phe Asn Lys
        195                 200                 205

GTG AAG GTG GAG GAC GCT GGA GAG TAC GTC TGT GAG GCT GAG AAC ATC    672
Val Lys Val Glu Asp Ala Gly Glu Tyr Val Cys Glu Ala Glu Asn Ile
210                 215                 220

CTT GGG AAG GAC ACT GTG AGG GGC CGG CTC CAT GTC AAC AGT GTG AGC    720
Leu Gly Lys Asp Thr Val Arg Gly Arg Leu His Val Asn Ser Val Ser
225                 230                 235                 240

ACC ACT CTG TCG TCC TGG TCG GGG CAC GCC CGG AAG TGC AAT GAG ACA    768
Thr Thr Leu Ser Ser Trp Ser Gly His Ala Arg Lys Cys Asn Glu Thr
                245                 250                 255

GCC AAG TCC TAC TGT GTG AAT GGA GGC GTG TGC TAC TAC ATC GAA GGC    816
Ala Lys Ser Tyr Cys Val Asn Gly Gly Val Cys Tyr Tyr Ile Glu Gly
            260                 265                 270

ATC AAC CAA CTC TCC TGC AAA TGT CCA AAC GGA TTC TTC GGA CAG AGA    864
Ile Asn Gln Leu Ser Cys Lys Cys Pro Asn Gly Phe Phe Gly Gln Arg
        275                 280                 285

TGT TTG GAG AAA CTG CCT TTG CGA TTG TAC ATG CCA GAT CCT AAG CAA    912
Cys Leu Glu Lys Leu Pro Leu Arg Leu Tyr Met Pro Asp Pro Lys Gln
290                 295                 300

AGT GTC CTG TGG GAT ACA CCG GGG ACA GGT GTC AGC AGT TCG CAA TGG    960
Ser Val Leu Trp Asp Thr Pro Gly Thr Gly Val Ser Ser Ser Gln Trp
305                 310                 315                 320

TCA ACT TCT CCA AGC ACC TTG GAT TTG AAT TAA                        993
Ser Thr Ser Pro Ser Thr Leu Asp Leu Asn
                325                 330

(2) INFORMATION FOR SEQ ID NO:4:

(i) SEQUENCE CHARACTERISTICS:
        (A) LENGTH: 330 amino acids
        (B) TYPE: amino acid
        (D) TOPOLOGY: linear (ii) MOLECULE TYPE: protein (xi) SEQUENCE DESCRIPTION: SEQ ID NO:4:

Met Arg Arg Asp Pro Ala Pro Gly Phe Ser Met Leu Leu Phe Gly Val
1               5                   10                  15

Ser Leu Ala Cys Tyr Ser Pro Ser Leu Lys Ser Val Gln Asp Gln Ala
            20                  25                  30

Tyr Lys Ala Pro Val Val Val Glu Gly Lys Val Gln Gly Leu Ala Pro
        35                  40                  45

Ala Gly Gly Ser Ser Ser Asn Ser Thr Arg Glu Pro Pro Ala Ser Gly
    50                  55                  60

Arg Val Ala Leu Val Lys Val Leu Asp Lys Trp Pro Leu Arg Ser Gly
65                  70                  75                  80

Gly Leu Gln Arg Glu Gln Val Ile Ser Val Gly Ser Cys Ala Pro Leu
                85                  90                  95

Glu Arg Asn Gln Arg Tyr Ile Phe Phe Leu Glu Pro Thr Glu Gln Pro
            100                 105                 110

Leu Val Phe Lys Thr Ala Phe Ala Pro Val Asp Pro Asn Gly Lys Asn
        115                 120                 125

Ile Lys Lys Glu Val Gly Lys Ile Leu Cys Thr Asp Cys Ala Thr Arg
    130                 135                 140

Pro Lys Leu Lys Lys Met Lys Ser Gln Thr Gly Glu Val Gly Glu Lys
145                 150                 155                 160

Gln Ser Leu Lys Cys Glu Ala Ala Gly Asn Pro Gln Pro Ser Tyr
                165                 170                 175
```

```
Arg Trp Phe Lys Asp Gly Lys Glu Leu Asn Arg Ser Arg Asp Ile Arg
            180                 185                 190

Ile Lys Tyr Gly Asn Gly Arg Lys Asn Ser Arg Leu Gln Phe Asn Lys
        195                 200                 205

Val Lys Val Glu Asp Ala Gly Glu Tyr Val Cys Glu Ala Glu Asn Ile
    210                 215                 220

Leu Gly Lys Asp Thr Val Arg Gly Arg Leu His Val Asn Ser Val Ser
225                 230                 235                 240

Thr Thr Leu Ser Ser Trp Ser Gly His Ala Arg Lys Cys Asn Glu Thr
                245                 250                 255

Ala Lys Ser Tyr Cys Val Asn Gly Val Cys Tyr Tyr Ile Glu Gly
            260                 265                 270

Ile Asn Gln Leu Ser Cys Lys Cys Pro Asn Gly Phe Phe Gly Gln Arg
        275                 280                 285

Cys Leu Glu Lys Leu Pro Leu Arg Leu Tyr Met Pro Asp Pro Lys Gln
    290                 295                 300

Ser Val Leu Trp Asp Thr Pro Gly Thr Gly Val Ser Ser Ser Gln Trp
305                 310                 315                 320

Ser Thr Ser Pro Ser Thr Leu Asp Leu Asn
                325                 330
```

(2) INFORMATION FOR SEQ ID NO:5:

(i) SEQUENCE CHARACTERISTICS:
        (A) LENGTH: 1207 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 2..394

(xi) SEQUENCE DESCRIPTION: SEQ ID NO:5:

```
A AAG AAC TCA CGG CTA CAG TTC AAC AAA GTG AAG GTG GAG GAC GCT           46
  Lys Asn Ser Arg Leu Gln Phe Asn Lys Val Lys Val Glu Asp Ala
   1               5                  10                  15

GGA GAG TAC GTC TGT GAG GCT GAG AAC ATC CTT GGG AAG GAC ACT GTG         94
Gly Glu Tyr Val Cys Glu Ala Glu Asn Ile Leu Gly Lys Asp Thr Val
                 20                  25                  30

AGG GGC CGG CTC CAT GTC AAC AGT GTG AGC ACC ACT CTG TCG TCC TGG        142
Arg Gly Arg Leu His Val Asn Ser Val Ser Thr Thr Leu Ser Ser Trp
             35                  40                  45

TCG GGG CAC GCC CGG AAG TGC AAT GAG ACA GCC AAG TCC TAC TGT GTG        190
Ser Gly His Ala Arg Lys Cys Asn Glu Thr Ala Lys Ser Tyr Cys Val
         50                  55                  60

AAT GGA GGC GTG TGC TAC TAC ATC GAA GGC ATC AAC CAA CTC TCC TGC        238
Asn Gly Gly Val Cys Tyr Tyr Ile Glu Gly Ile Asn Gln Leu Ser Cys
     65                  70                  75

AAA TGT CCA AAC GGA TTC TTC GGA CAG AGA TGT TTG GAG AAA CTG CCT        286
Lys Cys Pro Asn Gly Phe Phe Gly Gln Arg Cys Leu Glu Lys Leu Pro
 80                  85                  90                  95

TTG CGA TTG TAC ATG CCA GAT CCT AAG CAA AGT GTC CTG TGG GAT ACA        334
Leu Arg Leu Tyr Met Pro Asp Pro Lys Gln Ser Val Leu Trp Asp Thr
                100                 105                 110

CCG GGG ACA GGT GTC AGC AGT TCG CAA TGG TCA ACT TCT CCA AGC ACC        382
Pro Gly Thr Gly Val Ser Ser Ser Gln Trp Ser Thr Ser Pro Ser Thr
            115                 120                 125
```

-continued

```
TTG GAT TTG AAT TAAAGGAGGC TGAGGAGCTG TACCAGAAGA GAGTCCTGAC         434
Leu Asp Leu Asn
        130

AATTACCGGC ATCTGTGTGG CTCTGCTGGT CGTGGGCATC GTCTGTGTGG TCGCCTACTG    494

CAAGACTAAA AAACAGAGGA GGCAAATGCA TCACCATCTC CGGCAGAACA TGTGTCCGGC   554

CCACCAGAAC CGAAGCCTGG CCAATGGGCC CAGCCACCCT CGGCTGGACC CTGAGGAGAT   614

CCAGATGGCA GATTACATTT CCAAAAATGT GCCAGCTACA GACCATGTGA TCCGGAGGGA   674

AGCTGAGACC ACATTTTCTG GGAGCCACTC CTGTTCACCC TCTCACCACT GTTCCACAGC   734

CACACCCACC TCCAGCCACA GACATGAGAG CCACACGTGG AGCTTGGAAC GTTCGGAGAG   794

CCTGACCTCG GATTCCCAGT CAGGCATCAT GCTATCATCA GTGGGCACCA GCAAGTGCAA   854

CAGCCCAGCA TGTGTGGAGG CACGGGCACG GAGGGCAGCA GCCTACAGCC AGGAGGAGCG   914

ACGCAGGGCT GCCATGCCAC CCTACCACGA CTCCATAGAC TCGCTGCGTG ACTCCCCACA   974

CAGTGAGAGG TACGTGTCAG CCCTGACCAC GCCCGCGCGC CTTTCGCCCG TGGACTTCCA  1034

CTACTCGCTG GCCACCCAGG TGCCGACTTT CGAGATCACG TCGCCCAACT CTGCCCACGC  1094

CGTGTCGCTG CCACCCGCAG CGCCCATCAG CTACCGCCTA GCGGAGCAGC AGCCGCTCCT  1154

GGGGCACCCA GCGCCGCCCG GCCCGGGGCC AGGGCCCGGA GCGGACATGC AGC          1207
```

(2) INFORMATION FOR SEQ ID NO:6:

(i) SEQUENCE CHARACTERISTICS:
        (A) LENGTH: 131 amino acids
        (B) TYPE: amino acid
        (D) TOPOLOGY: linear (ii) MOLECULE TYPE: protein (xi) SEQUENCE DESCRIPTION: SEQ ID NO:6:

```
Lys Asn Ser Arg Leu Gln Phe Asn Lys Val Lys Val Glu Asp Ala Gly
1               5                  10                  15

Glu Tyr Val Cys Glu Ala Glu Asn Ile Leu Gly Lys Asp Thr Val Arg
            20                  25                  30

Gly Arg Leu His Val Asn Ser Val Ser Thr Thr Leu Ser Ser Trp Ser
        35                  40                  45

Gly His Ala Arg Lys Cys Asn Glu Thr Ala Lys Ser Tyr Cys Val Asn
    50                  55                  60

Gly Gly Val Cys Tyr Tyr Ile Glu Gly Ile Asn Gln Leu Ser Cys Lys
65                  70                  75                  80

Cys Pro Asn Gly Phe Phe Gly Gln Arg Cys Leu Glu Lys Leu Pro Leu
                85                  90                  95

Arg Leu Tyr Met Pro Asp Pro Lys Gln Ser Val Leu Trp Asp Thr Pro
            100                 105                 110

Gly Thr Gly Val Ser Ser Gln Trp Ser Thr Ser Pro Ser Thr Leu
        115                 120                 125

Asp Leu Asn
        130
```

(2) INFORMATION FOR SEQ ID NO:7:

(i) SEQUENCE CHARACTERISTICS:
        (A) LENGTH: 40 amino acids
        (B) TYPE: amino acid
        (D) TOPOLOGY: linear (ii) MOLECULE TYPE: peptide (v) FRAGMENT TYPE: internal

```
   (ix) FEATURE:
        (A) NAME/KEY: Modified-site
        (B) LOCATION: 2-8
        (D) OTHER INFORMATION: /note= "Xaa is any amino acid"

(ix) FEATURE:
        (A) NAME/KEY: Modified-site
        (B) LOCATION: 10-13
        (D) OTHER INFORMATION: /note= "Xaa is any amino acid"

(ix) FEATURE:
        (A) NAME/KEY: Modified-site
        (B) LOCATION: 14
        (D) OTHER INFORMATION: /note= "Xaa, if present, is any amino
                                        acid"

(ix) FEATURE:
        (A) NAME/KEY: Modified-site
        (B) LOCATION: 16-25
        (D) OTHER INFORMATION: /note= "Xaa is any amino acid"

(ix) FEATURE:
        (A) NAME/KEY: Modified-site
        (B) LOCATION: 26, 27, 28
        (D) OTHER INFORMATION: /note= "Xaa, if present, is any amino
                                        acid"

(ix) FEATURE:
        (A) NAME/KEY: Modified-site
        (B) LOCATION: 30
        (D) OTHER INFORMATION: /note= "Xaa is any amino acid"

(ix) FEATURE:
        (A) NAME/KEY: Modified-site
        (B) LOCATION: 32-39
        (D) OTHER INFORMATION: /note= "Xaa is any amino acid"

(xi) SEQUENCE DESCRIPTION: SEQ ID NO:7:

Cys Xaa Xaa Xaa Xaa Xaa Xaa Xaa Cys Xaa Xaa Xaa Xaa Cys Xaa
    1               5                  10                  15

Xaa Xaa Xaa Xaa Xaa Xaa Xaa Xaa Xaa Xaa Xaa Xaa Cys Xaa Cys Xaa
                    20                  25                  30

Xaa Xaa Xaa Xaa Xaa Xaa Xaa Cys
            35                  40

(2) INFORMATION FOR SEQ ID NO:8:

(i) SEQUENCE CHARACTERISTICS:
        (A) LENGTH: 57 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 2-5
        (D) OTHER INFORMATION: /note= "Xaa is any amino acid"

(ix) FEATURE:
        (A) NAME/KEY: Modified-site
        (B) LOCATION: 6, 7, 8, 9, 10, 11, 12, 13, 14, 15
        (D) OTHER INFORMATION: /note= "Xaa, if present, is any amino
                                        acid"

(ix) FEATURE:
        (A) NAME/KEY: Modified-site
        (B) LOCATION: 17-19
        (D) OTHER INFORMATION: /note= "Xaa is any amino acid"

(ix) FEATURE:
        (A) NAME/KEY: Modified-site
        (B) LOCATION: 20, 21, 22, 23, 24
```

(D) OTHER INFORMATION: /note= "Xaa, if present, is any amino
                acid"

(ix) FEATURE:
         (A) NAME/KEY: Modified-site
         (B) LOCATION: 26-29
         (D) OTHER INFORMATION: /note= "Xaa is any amino acid"

(ix) FEATURE:
         (A) NAME/KEY: Modified-site
         (B) LOCATION: 30, 31, 32, 33, 34, 35, 36, 37, 38,39
         (D) OTHER INFORMATION: /note= "Xaa, if present, is any amino
                acid"

(ix) FEATURE:
         (A) NAME/KEY: Modified-site
         (B) LOCATION: 41
         (D) OTHER INFORMATION: /note= "Xaa is any amino acid"

(ix) FEATURE:
         (A) NAME/KEY: Modified-site
         (B) LOCATION: 43-50
         (D) OTHER INFORMATION: /note= "Xaa is any amino acid"

(ix) FEATURE:
         (A) NAME/KEY: Modified-site
         (B) LOCATION: 51, 52, 53, 54, 55, 56
         (D) OTHER INFORMATION: /note= "Xaa, if present, is any amino
                acid"

(xi) SEQUENCE DESCRIPTION: SEQ ID NO:8:

Cys Xaa Xaa Xaa Xaa Xaa Xaa Xaa Xaa Xaa Xaa Xaa Xaa Xaa Xaa Cys
1               5                   10                  15

Xaa Xaa Xaa Xaa Xaa Xaa Xaa Xaa Cys Xaa Xaa Xaa Xaa Xaa Xaa
            20                  25                  30

Xaa Xaa Xaa Xaa Xaa Xaa Xaa Cys Xaa Cys Xaa Xaa Xaa Xaa Xaa Xaa
        35                  40                  45

Xaa Xaa Xaa Xaa Xaa Xaa Xaa Xaa Cys
    50                  55

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:9:

ATGCTCGCCT GCTACTCGCC C                                              21

(2) INFORMATION FOR SEQ ID NO:10:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:10:

GCCGGACACA TGTTCTGCC                                                 19

(2) INFORMATION FOR SEQ ID NO:11:

(i) SEQUENCE CHARACTERISTICS:
        (A) LENGTH: 19 base pairs
        (B) TYPE: nucleic acid (C) STRANDEDNESS: single
        (D) TOPOLOGY: linear (ii) MOLECULE TYPE: oligonucleotide (xi) SEQUENCE DESCRIPTION: SEQ ID NO:11:

CACTGACTGC GCAACCCGG                                                        19

(2) INFORMATION FOR SEQ ID NO:12:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:12:

GGCCTTAGAG GGGCCCGGA                                                        19

(2) INFORMATION FOR SEQ ID NO:13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:13:

AAAGAACTCA CGGCTACAGT TC                                                    22

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:14:

CCTTTAATTC AAATCCAAGG T                                                     21

(2) INFORMATION FOR SEQ ID NO:15:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:15:

GAATTCGGCA CGAGGGCAG                                                        19

(2) INFORMATION FOR SEQ ID NO:16:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:16:

CTCATTGCAC TTCCGGGCG                                              19

(2) INFORMATION FOR SEQ ID NO:17:

(i) SEQUENCE CHARACTERISTICS:
        (A) LENGTH: 65 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:17:

AGGCGTGTGC TACTACATCG AAGGCATCAA CCAACTCTCC TGCAAGTGTC CTGTGGGATA    60

CACCG                                                              65

(2) INFORMATION FOR SEQ ID NO:18:

(i) SEQUENCE CHARACTERISTICS:
        (A) LENGTH: 142 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:18:

AGGCGTGTGC TACTACATCG AAGGCATCAA CCAACTCTCC TGCAAATGTC CAAACGGATT    60

CTTCGGACAG AGATGTTTGG AGAAACTGCC TTTGCGATTG TACATGCCAG ATCCTAAGCA   120

AAGTGTCCTG TGGGATACAC CG                                          142